United States Patent
Griffiths et al.

(10) Patent No.: US 11,000,457 B2
(45) Date of Patent: *May 11, 2021

(54) MAKEUP REPAIR SYSTEM, KIT, METHOD, AND TOOLS

(71) Applicants: Tess Griffiths, Los Angeles, CA (US); Barbara Villegas, Los Angeles, CA (US)

(72) Inventors: Tess Griffiths, Los Angeles, CA (US); Barbara Villegas, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/629,727

(22) Filed: Jun. 21, 2017

(65) Prior Publication Data

US 2018/0338889 A1  Nov. 29, 2018

Related U.S. Application Data

(63) Continuation-in-part of application No. 29/606,002, filed on May 31, 2017, now Pat. No. Des. 846,801.
(Continued)

(51) Int. Cl.
*A45D 33/00* (2006.01)
*B29C 43/36* (2006.01)
*A61K 8/02* (2006.01)

(52) U.S. Cl.
CPC .......... *A61K 8/022* (2013.01); *A45D 33/006* (2013.01); *A45D 33/003* (2013.01);
(Continued)

(58) Field of Classification Search
CPC .. A45D 33/001; A45D 33/003; A45D 33/006; B29C 43/00; B29C 43/02
(Continued)

(56) References Cited

U.S. PATENT DOCUMENTS 1,711,798 A  5/1929 Kronish
1,731,219 A  10/1929 Atwood
(Continued)

FOREIGN PATENT DOCUMENTS

KR  300756487  8/2014
KR  300756488  8/2014
(Continued)

OTHER PUBLICATIONS

Coffee tamper product available from: https://www.bedbathandbeyond.com/store/product/rsvp-espresso-tamper/1045959158skuId=45959158&mcid=PS_googlepla_nonbrand_kitchenelectrics_&adpos=1o1&creative=43742642989&device=c&matchtype=&network=s&product_id=45959158&gclid=CPG08tfvmNQCFQyAfgodZtkAmg (last visited on May 30, 2017); see attached and including copy of non patent literature showing screenshot of this coffee tamper.
(Continued)

*Primary Examiner* — Thu Khanh T Nguyen
(74) *Attorney, Agent, or Firm* — Eric Kelly

(57) ABSTRACT

Tools, systems, kits, and methods for both repairing and refreshing cosmetic makeups are discussed. One such tool may be a spatula. Other such tools may be press tools for pressing and compacting makeup. In some embodiments, such press tools may be double ended, with two different sized and/or different shaped presses per given press tool, with a handle between such different sized and/or such different shaped presses, to accommodate different sized and different shaped makeup pans. A container with repair-mousse, of a predetermined formula, may be used to treat broken and/or un-fresh makeup to repair and/or refresh such makeup to a desired consistency.

18 Claims, 20 Drawing Sheets

Related U.S. Application Data and a continuation-in-part of application No. 15/606,802, filed on May 26, 2017.

(52) U.S. Cl.
CPC .... *A45D 2033/001* (2013.01); *A45D 2200/25* (2013.01); *A61K 2800/10* (2013.01); *A61K 2800/80* (2013.01)

(58) Field of Classification Search
USPC .................................................. 425/318, 412
See application file for complete search history.

(56) References Cited

U.S. PATENT DOCUMENTS

| | | | |
|---|---|---|---|
| 2,074,795 | A | 3/1937 | Mantelet |
| 2,994,262 | A | 8/1961 | Bator |
| 3,222,030 | A | 12/1965 | Thorpe |
| D223,689 | S | 5/1972 | Forbes |
| D232,280 | S | 8/1974 | Bingham |
| D249,910 | S | 10/1978 | Cottrell |
| D249,911 | S | 10/1978 | Cottrell |
| D261,346 | S * | 10/1981 | Thornley .................. D7/412 |
| D283,856 | S | 5/1986 | Elmaleh |
| D295,004 | S | 4/1988 | Schulz |
| D298,597 | S | 11/1988 | Bell |
| D319,556 | S | 9/1991 | Purkapile |
| D338,310 | S | 8/1993 | Clarke |
| D340,822 | S | 11/1993 | Morand |
| D341,856 | S | 11/1993 | Silverman |
| D395,987 | S | 7/1998 | Loughead |
| D399,103 | S | 10/1998 | Lillelund |
| D404,947 | S | 2/1999 | Porcelli |
| D408,687 | S | 4/1999 | Chan |
| D432,828 | S | 10/2000 | Snell |
| 6,245,341 | B1 * | 6/2001 | Pahlck .................. A45D 33/00 424/401 |
| D446,979 | S | 8/2001 | Schultz |
| 6,358,448 | B1 * | 3/2002 | Green .................. A45D 33/006 425/318 |
| D455,948 | S | 4/2002 | Zetsche |
| D457,271 | S | 5/2002 | Jackson |
| D459,623 | S | 7/2002 | Tramontina |
| D470,759 | S | 2/2003 | Thorne |
| 6,612,533 | B2 | 9/2003 | Biles |
| D485,742 | S | 1/2004 | Heberle |
| D498,099 | S | 11/2004 | Chen |
| D504,307 | S | 4/2005 | Dayan |
| D531,863 | S | 11/2006 | Irwin |
| D540,585 | S | 4/2007 | Igarashi |
| D545,343 | S | 6/2007 | Braun |
| D549,085 | S | 8/2007 | Mevissen |
| D567,023 | S | 4/2008 | Baldieri |
| D610,869 | S | 3/2010 | Pourounidis |
| D625,528 | S | 10/2010 | Sprague |
| 8,038,118 | B1 * | 10/2011 | Ajakie .................. A47J 43/20 249/156 |
| D693,596 | S | 11/2013 | Zeng |
| D707,056 | S | 6/2014 | Gilbert |
| D718,896 | S | 12/2014 | Foley |
| D754,401 | S | 4/2016 | Seiler |
| D765,262 | S | 8/2016 | Greenhouse |
| D776,453 | S | 1/2017 | Cross |
| D815,167 | S | 4/2018 | Lin |
| D817,119 | S * | 5/2018 | Hand .................. D7/677 |
| D821,598 | S | 6/2018 | Greenhouse |
| D821,599 | S | 6/2018 | Greenhouse |
| 10,004,938 | B2 | 6/2018 | Greenhouse |
| D823,624 | S | 7/2018 | Elmaleh |
| 2003/0235470 | A1 | 12/2003 | Gelb |
| 2013/0234351 | A1 | 9/2013 | Johnson |
| 2017/0065515 | A1 | 3/2017 | Karam |
| 2017/0223972 | A1 | 8/2017 | Hotz |

FOREIGN PATENT DOCUMENTS

| | | |
|---|---|---|
| KR | 300839937 | 2/2016 |
| KR | 300931268 | 11/2017 |

OTHER PUBLICATIONS

Coffee tamper product available from: http://www.simplygreatcoffee.co.uk/shop/black-plastic-double-sided-tamper-48mm-57mm (last visited on May 30, 2017); see attached and included copy of non patent literature showing screenshot of this coffee tamper.

Coffee tamper product available from: http://www.1st-line.com/store/pc/Ascaso-Tamper-Nylon-Plastic-p4333.htm (last visited on May 30, 2017); see attached and included copy of non patent literature showing screenshot of this coffee tamper.

Coffee tamper product available from: https://www.bedbathandbeyond.com/store/product/rsvp-espresso-tamper/104595915 8skuld=45959158&mcid=PS_googlepla_nonbrand_kitchenelectrics_&adpos=1o1&creative=43742642989&device=c&matchtype=&network=s&product_id=45959158&gclid=CPG08tfvmNQCFQyAfgodZtkAmg (last visited on May 30, 2017); see attached and included copy of non patent literature showing screenshot of this coffee tamper.

Steel Tamping and Digging Bar, Bully Tools, homedepot.com, author unlisted, posted Oct. 11, 2014 per wayback machine; available at URL: https:www.homedepot.com/p/Bully-Tools-48-in-Steel-Tamping-and-Digging-Bar-9244 (Year: 2014).

Square and Rectangle Pedestal Base, David Lane Office Furniture, Ltd., davidlane.com, author not listed, posted Apr. 2, 2018 per wayback machine. Available from Internet, URL: https://www.davidlane.com/metal/ (Year: 2018).

* cited by examiner

MAKEUP REPAIR SYSTEM, KIT, METHOD, AND TOOLS

PRIORITY NOTICE

The present patent application is a continuation-in-part (CIP) of U.S. non-provisional patent application Ser. No. 15/606,802 filed on May 26, 2017; wherein this present patent application claims priority to said U.S. non-provisional patent application under 35 U.S.C. § 120. The above-identified parent U.S. non-provisional patent application is incorporated herein by reference in their entirety as if fully set forth below.

The present patent application is a continuation-in-part (CIP) of U.S. non-provisional patent application Ser. No. 29/606,002 filed on May 31, 2017; wherein this present patent application claims priority to said U.S. non-provisional patent application under 35 U.S.C. § 120. The above-identified parent U.S. non-provisional patent application is incorporated herein by reference in their entirety as if fully set forth below.

TECHNICAL FIELD OF THE INVENTION

The present invention relates to tools, systems, kits, and methods for both repairing and refreshing cosmetic makeups.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Cosmetics makeup, such as powders, mineral based makeups, blush, foundation, bronzers, concealers, eyeliners, mascaras, creams, nail polish, and the like, are often expensive; yet, also are often prone to being broken and/or becoming un-fresh; either one of which may result in a waste of money any money.

For example, and particularly with respect to powder based makeups, if accidentally dropped, the preferred consistency of the powder based makeup may be fractured, spilled, and/or otherwise disturbed, such that the resulting broken-makeup may now no longer be properly used; potentially resulting in the waste of money and time.

Similarly, whether broken or not, as makeup ages and/or is exposed to environmental conditions, such as humidity and air, that exposed makeup may become un-fresh and thus less desirable to use.

There is then a need in the art for tools, systems, kits, and methods for repairing such broken-makeup, so that once repaired, the now repaired makeup may be readily used again; without needing to purchase new makeup.

And likewise, there is a need in the art for tools, systems, kits, and methods for refreshing un-fresh makeup, so that once refreshed, the now refreshed makeup may be readily used again.

It is to these ends that the present invention has been developed.

BRIEF SUMMARY OF THE INVENTION

To minimize the limitations in the prior art, and to minimize other limitations that will be apparent upon reading and understanding the present specification, embodiments of the present invention may describe tools, systems, kits, and methods for both repairing and/or refreshing cosmetic makeups. In some embodiments, one such tool may be a spatula. Other such tools may be press tools, denoted herein as makeup-repair-tool(s), for pressing and compacting makeup. In some embodiments, such makeup-repair-tools may be double ended, with two different sized and/or different shaped presses per given makeup-repair-tool, with a handle between such different sized and/or such different shaped presses, to accommodate different sized and different shaped makeup pans. A container with repair-mousse, of a predetermined formula, may be used to treat broken and/or un-fresh makeup to repair and/or refresh such makeup to a desired consistency.

It is an objective of the present invention to provide tools for assisting in the repair of broken makeup.

It is another objective of the present invention to provide tools for assisting in the refreshing of un-fresh makeup.

It is another objective of the present invention to provide press tools for pressing and/or compacting makeup.

It is another objective of the present invention to provide press tools with shapes and sizes configured to fit shapes and sizes of makeup pans.

It is another objective of the present invention to provide a single makeup-repair-tool with dual ended press tools; wherein each respective press tool may have its own shape and size; which may be different from each other, to accommodate different shapes and sizes of makeup pans.

It is another objective of the present invention to provide spatula tools for assisting in the repair of broken makeup.

It is another objective of the present invention to provide spatula tools for assisting in refreshing of un-fresh makeup.

It is another objective of the present invention to provide a repair-mousse of a predetermined formula and/or composition for assisting in the repairing of broken makeup.

It is another objective of the present invention to provide a repair-mousse of a predetermined formula and/or composition for assisting in the refreshing of un-fresh makeup.

It is another objective of the present invention to be able to manufacture such tools in a simple and cost effective way, which lends itself to mass production and economies of scale.

It is another objective of the present invention to provide systems for repairing and/or refreshing makeup.

It is another objective of the present invention to provide kits for repairing and/or refreshing makeup.

It is yet another objective of the present invention to provide methods of use for repairing and/or refreshing makeup.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

Figure 1A:
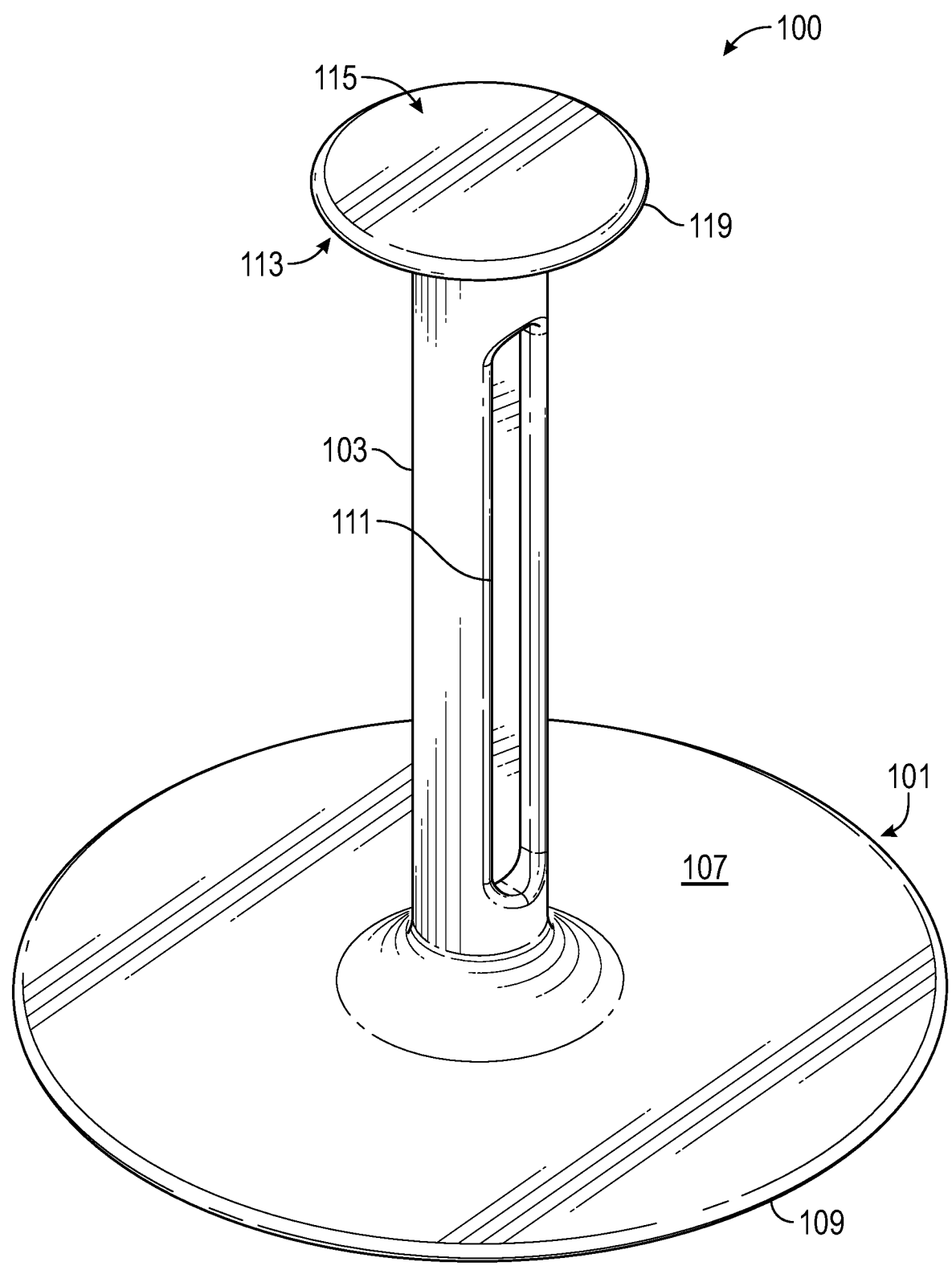
FIG. 1A may depict a top perspective view of a makeup-repair-tool according to a first embodiment.

REFERENCE NUMERAL SCHEDULE 100 makeup-repair-tool 100
101 first-press 101
103 handle 103
105 first-press-surface 105
107 first-non-press-surface 107
109 closed-perimeter 109
111 slot 111
113 second-press 113
115 second-press-surface 115
117 second-non-press-surface 117
119 second-closed-perimeter 119
121 dimension-of-first-press 121
123 dimension-of-second-press 123
200 makeup-repair-tool 200
201 first-press 201
203 handle 203
205 first-press-surface 205
207 first-non-press-surface 207
209 closed-perimeter 209
211 slot 211
213 second-press 213
215 second-press-surface 215
217 second-non-press-surface 217
219 second-closed-perimeter 219
221 dimension-of-first-press 221
223a dimension-of-second-press 223a
223b dimension-of-second-press 223b
300 spatula 300
400 method 400
405 step of preparing makeup pan 405
410 step of dispensing repair-mousse onto makeup 410
415 step of waiting for repair-mousse to absorb into the makeup 415
420 step of testing consistency of makeup 420
425 step of smoothing makeup 425
430 step of waiting a predetermined period of time 430
435 step of pressing makeup using makeup-repair-tool 435
440 step of drying the repaired makeup 440
450 method 450
460 method 460
501 makeup container 501
503 makeup pan 503
505 fragment-of-makeup 505
507 broken-makeup 507
509 normal-makeup 509
511 container 511
513 repair-mousse 513
515 damp-makeup 515

DETAILED DESCRIPTION OF THE INVENTION

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Figure 1B:
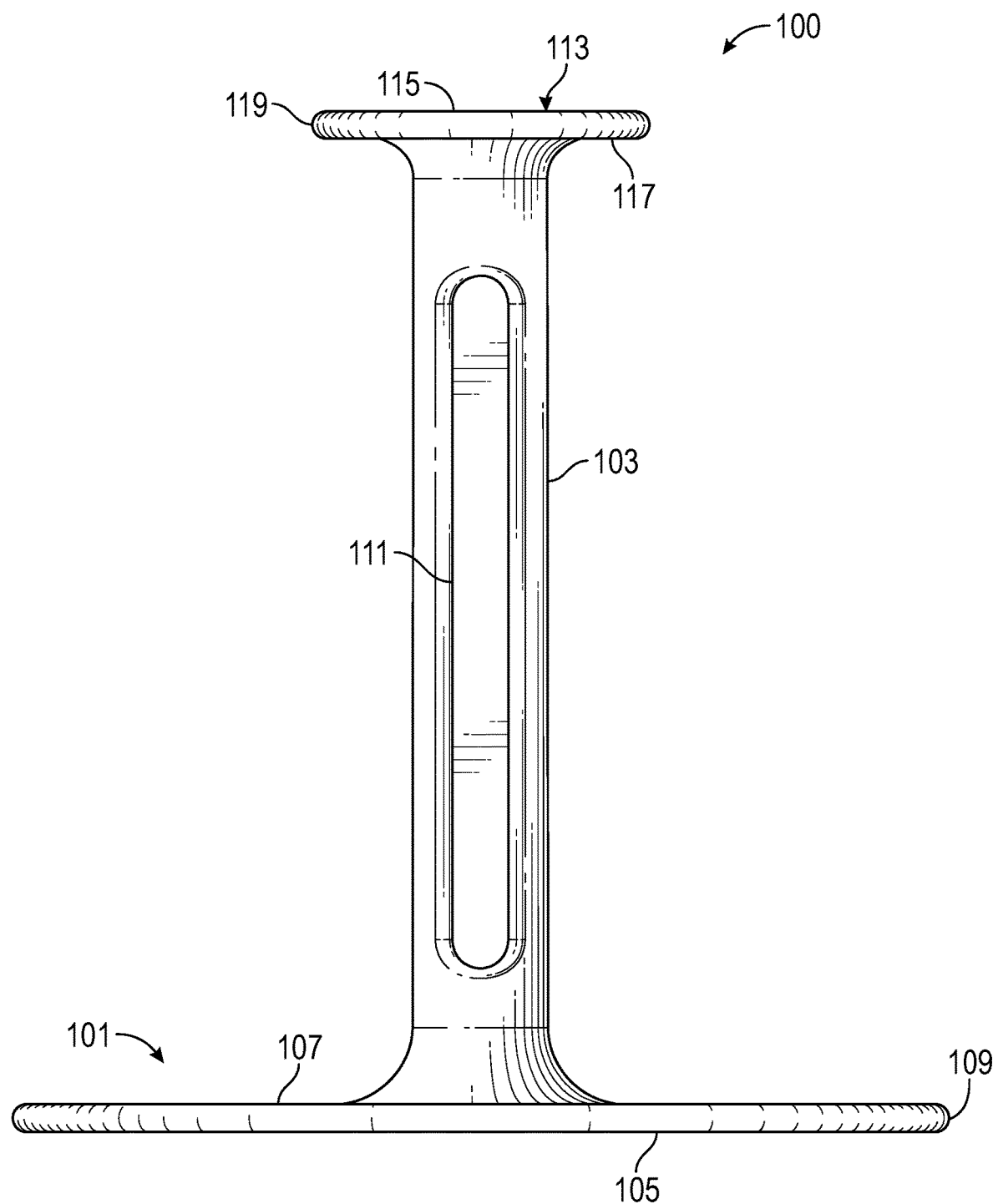
FIG. 1B may depict a front view and a back view of the makeup-repair-tool of FIG. 1A.
Figure 1C:
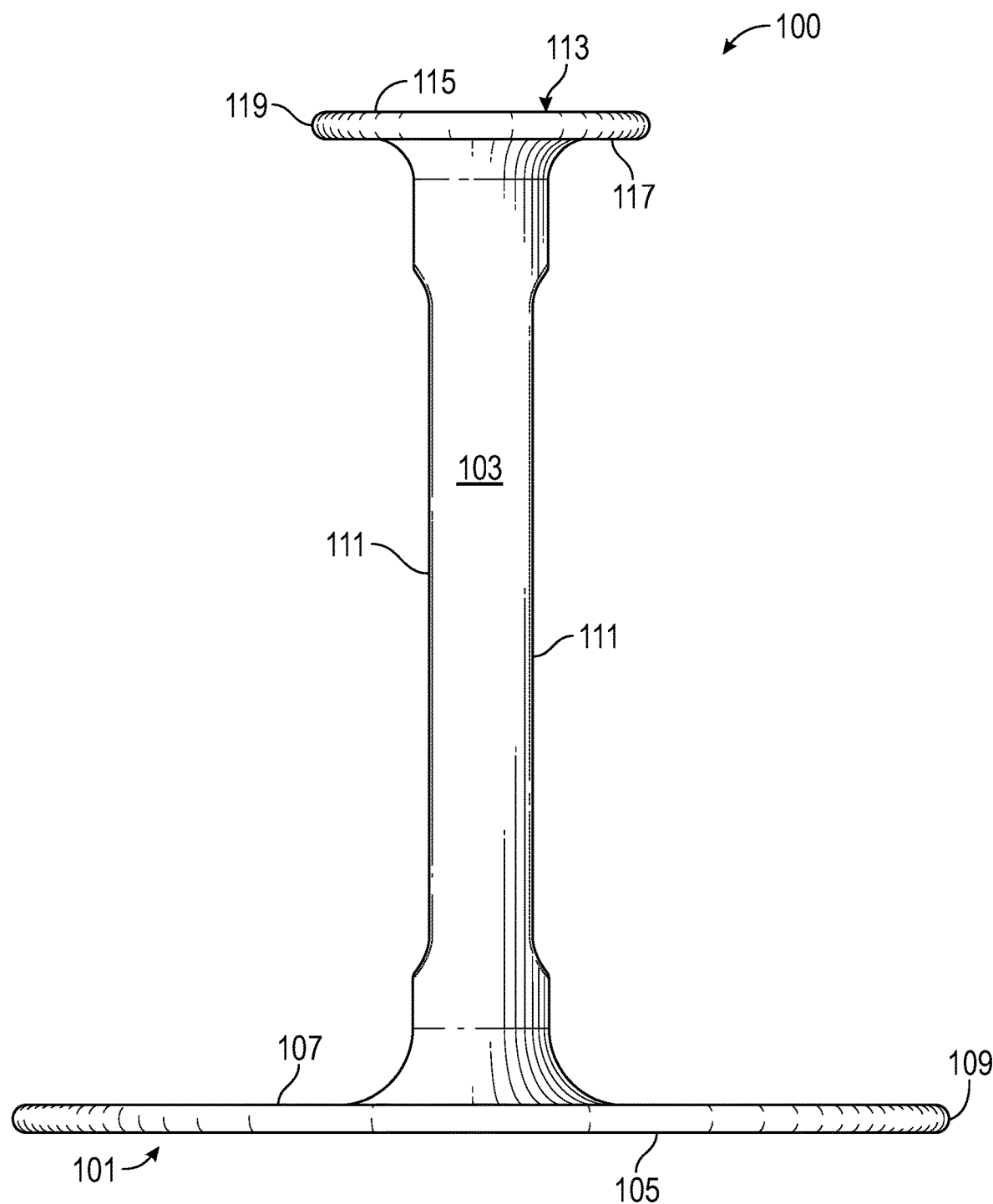
FIG. 1C may depict a left-side view and/or a right-side view of the makeup-repair-tool of FIG. 1A.
Figure 1D:
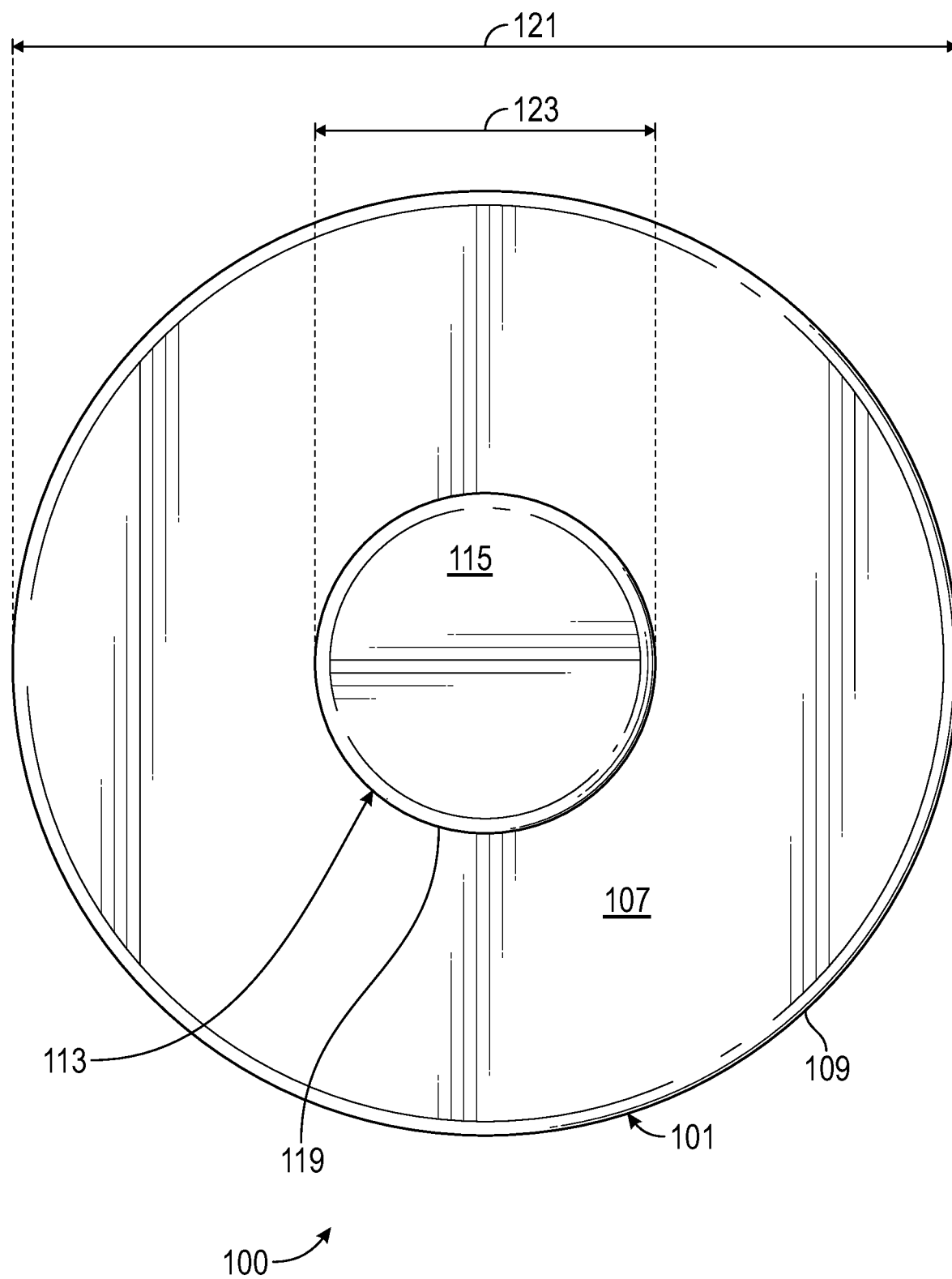
FIG. 1D may depict a top view of the makeup-repair-tool of FIG. 1A.
Figure 1E:
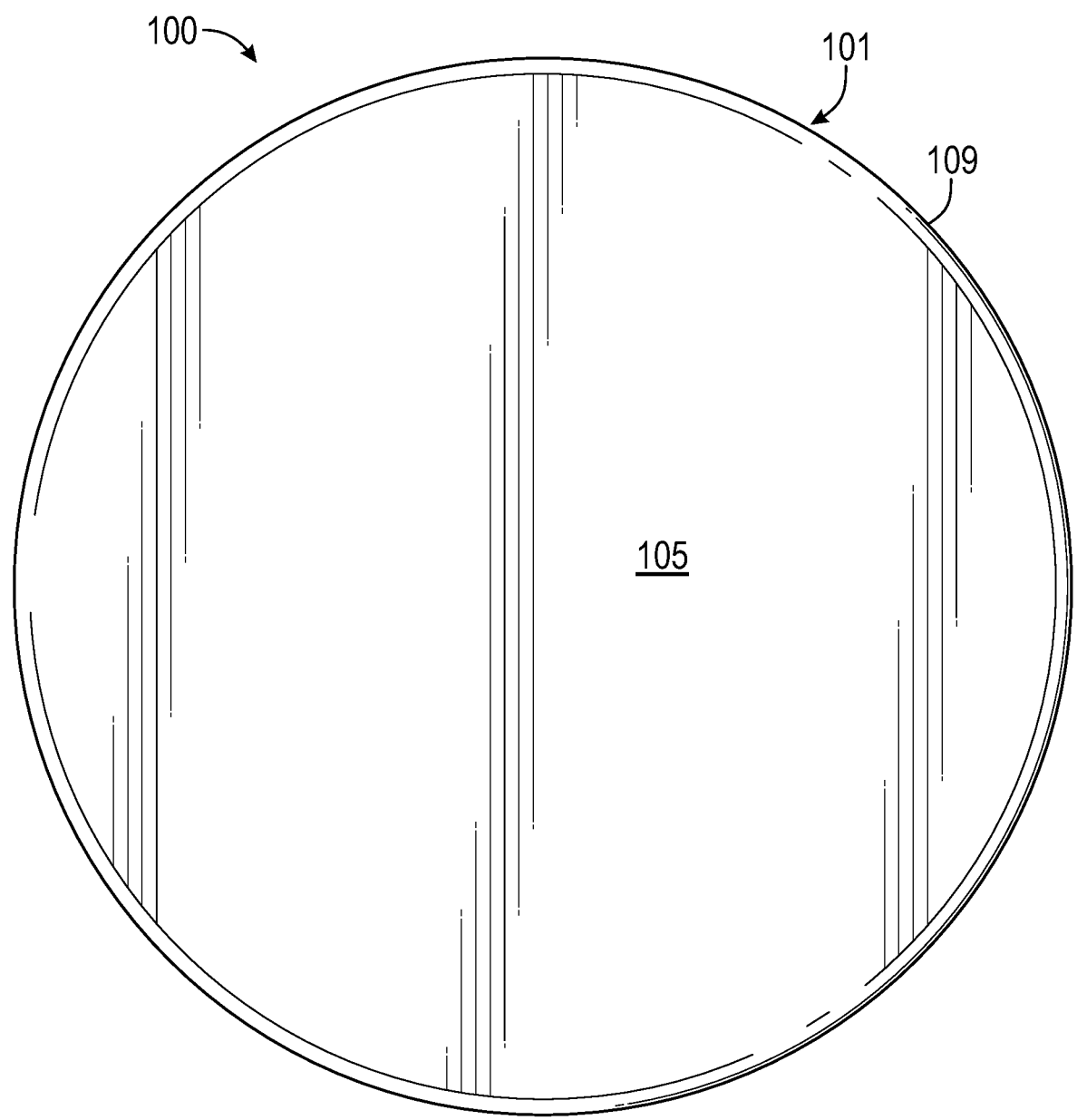
FIG. 1E may depict a bottom view of the makeup-repair-tool of FIG. 1A.
Figure 1F:
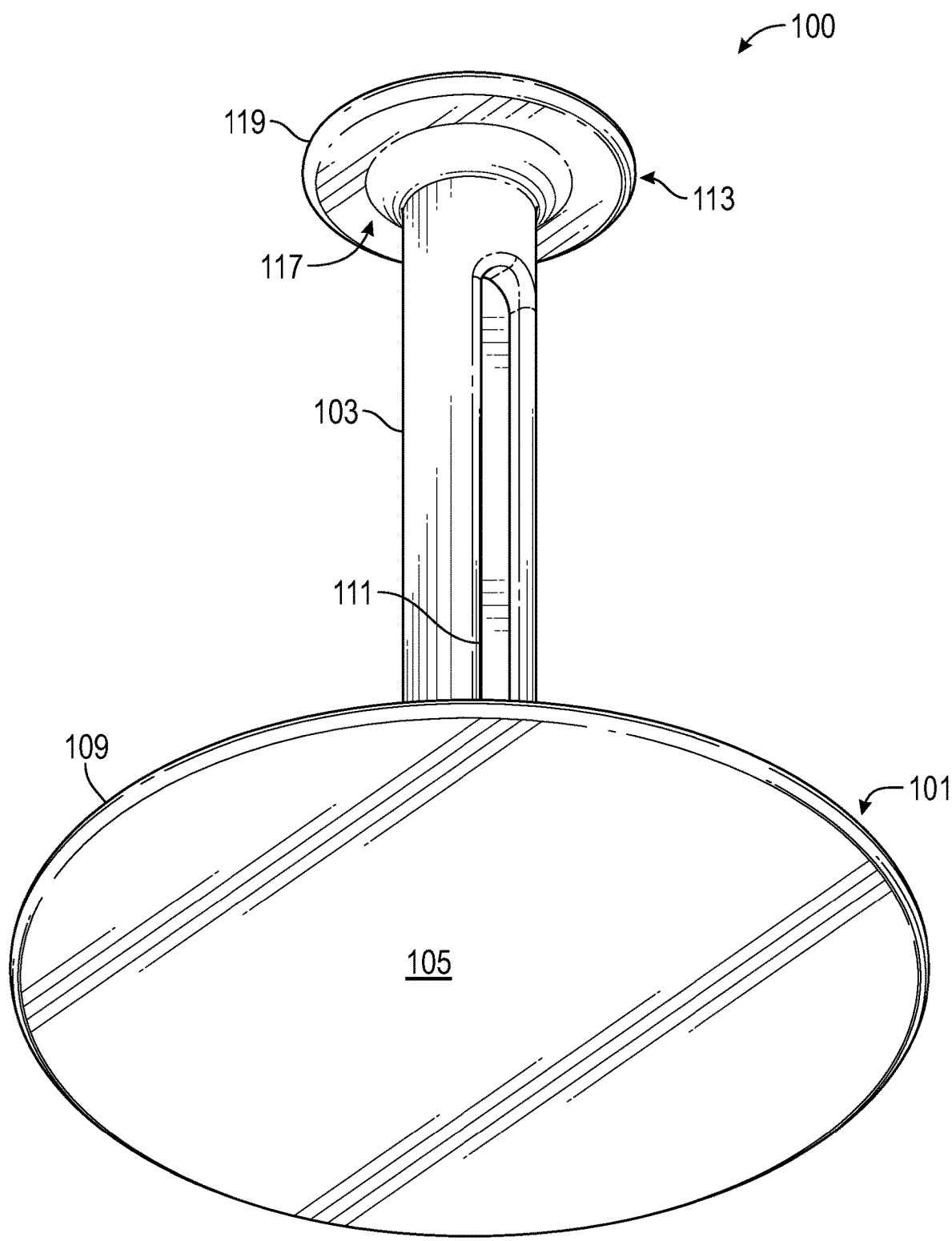
FIG. 1F may depict a bottom perspective view of the makeup-repair-tool of FIG. 1A.

FIG. 1A may depict a top perspective view of a makeup-repair-tool 100 according to a first embodiment. FIG. 1B may depict a front view and/or a back view of makeup-repair-tool 100. In some embodiments, the front view and the back view may be substantially similar or substantially identical. FIG. 1C may depict a left-side view and/or a right-side view of makeup-repair-tool 100. In some embodiments, the left-side view and the right-side view may be substantially similar or substantially identical. FIG. 1D may depict a top view of makeup-repair-tool 100. FIG. 1E may depict a bottom view of makeup-repair-tool 100. FIG. 1F may depict a bottom perspective view of makeup-repair-tool 100.

Discussing FIG. 1A, FIG. 1B, FIG. 1C, and FIG. 1F, in some embodiments, makeup-repair-tool 100 may comprise a first-press 101 and a handle 103. In some embodiments, first-press 101 may be for pressing against makeup to compact and level the makeup. See e.g., FIG. 5E for an example of such a use. In some embodiments, this makeup may be broken-makeup 507. Continuing discussing FIG. 1A, FIG. 1B, FIG. 1C, and FIG. 1F, in some embodiments, handle 103 may be attached to first-press 101. In some embodiments, when a force may be removably exerted upon handle 103, then first-press 101 may press against the makeup (e.g., against the broken-makeup 507). In some embodiments, when a force may be removably exerted upon handle 103, then first-press 101 may press against broken-makeup 507 to level and compact it, as may be illustrated in FIG. 5E.

In some embodiments, first-press 101 may comprise a first-press-surface 105 (see e.g., FIG. 1B, FIG. 1C, FIG. 1E, and FIG. 1F). In some embodiments, first-press 101 may comprise a first-non-press-surface 107 (see e.g., FIG. 1A, FIG. 1B, FIG. 1C, and FIG. 1D). In some embodiments, first-press-surface 105 may be disposed opposite of first-non-press-surface 107. In some embodiments, first-press-surface 105 and/or first-non-press-surface 107 may be major surface(s) of first-press 101 (e.g., as measured by surface area of first-press 101). In some embodiments, at least portions of first-press-surface 105 may removably contact the makeup (e.g., the broken-makeup 507). In some embodiments, handle 103 may attach to first-press 101 at at least one location of first-non-press-surface 107, see e.g., FIG. 1A, FIG. 1B, and FIG. 1C. This at least one location of attachment may be about a geometric center of first-non-press-surface 107.

In some embodiments, first-press-surface 105 may be one or more of substantially: electrostatically neutral, smooth, flat, planar, rigid, semi-rigid, textured, combinations thereof, and/or the like. See e.g., FIG. 1B, FIG. 1C, FIG. 1E, and FIG. 1F. Having a smooth, flat, planar, rigid, and/or semi-rigid characteristic of first-press-surface 105 may promote pressing and compacting of the makeup (such as against broken-makeup 507). Having an electrostatically neutral first-press-surface 105, may minimize such makeup "sticking" to first-press-surface 105 due to opposite electrical charges, as may otherwise occur in static electricity environments. In some embodiments, first-press-surface 105 or first-press 101 may be manufactured from a substantially electrostatically neutral material.

In some embodiments, first-press 101 may be defined and bound by a closed-perimeter 109. See e.g., FIG. 1A, FIG. 1B, FIG. 1C, FIG. 1D, FIG. 1E, and FIG. 1F. In some embodiments, this closed-perimeter 109 may be substantially circular. In some embodiments, this closed-perimeter 109 may be substantially shaped as: a circle, a polygon, a parallelogram, a rectangle, a square; and/or the like. In some embodiments, this closed-perimeter 109 may be substantially shaped and sized to fit within a makeup pan 503 that may be holding the makeup (such as holding the broken-makeup 503). A shape and size of a given makeup pan 503 is predetermined and fixed. In some embodiments, the makeup pan 503 may have an opening shaped substantially as: a circle, an oval, a polygon, a parallelogram, a rectangle, a square, an irregular polygon, a polygon with rounded corners, a star shape, and/or the like. See e.g., FIG. 5A through FIG. 5E which may show a circular shaped opening to makeup pan 503.

In some embodiments, handle 103 may be one or more of substantially: an elongate member, a structural member, a rigid member, a semi-rigid member, a straight member, combinations thereof, and/or the like. See e.g., FIG. 1A, FIG. 1B, FIG. 1C, and FIG. 1F. In some embodiments, handle 103 may be an elongate member that may extend substantially orthogonally from a major surface of first-press 101. See e.g., FIG. 1A, FIG. 1B, and FIG. 1C. In some embodiments, such a major surface may be first-non-press-surface 107.

In some embodiments, handle 103 may be an elongate member that may comprise at least one slot 111. In some embodiments, at least one slot 111 may run along at least some of a length of handle 103. In some embodiments, at least one slot 111 may have a longitude that may be substantially parallel with a longitude of the elongate member of handle 103. See e.g., FIG. 1A, FIG. 1B, FIG. 1C, and FIG. 1F.

In some embodiments, handle 103 may be an elongate member that may comprise two opposing slots 111. In some embodiments, these two opposing slots 111 may run along at least some of a length of handle 103. In some embodiments, these two opposing slots 111 each may have a longitude that may be substantially parallel with a longitude of the elongate member of handle 103. See e.g., FIG. 1A, FIG. 1B, FIG. 1C, and FIG. 1F.

In some embodiments, slot(s) 111 may reduce material costs in manufacturing a given handle 103 because such slot(s) 111 allow for void space. In some embodiments, slot(s) 111 may function as structural ribs or girders for a given handle 103, providing increased rigidity to handle 103 that otherwise would be absent in a handle without such slot(s) 111. In some embodiments, slot(s) 111 may function to reduce shrinkage problems from cooling post injection molding of a given handle 103 that otherwise would be absent in a handle without such slot(s) 111.

In some embodiments, makeup-repair-tool 100 may comprise a second-press 113. In some embodiments, second-press 113 may be attached to handle 103. In some embodiments, second-press 113 may be for pressing against different makeup; i.e., makeup within a different sized makeup pan 503 as compared against a makeup pan 503 that receives first-press 101. In some embodiments, when a different force may be removably exerted upon handle 103, then second-press 113 may press against the different makeup within the different sized makeup pan 503. See e.g., FIG. 1A, FIG. 1B, FIG. 1C, FIG. 1D, and FIG. 1F.

In some embodiments, second-press 113 may comprise a second-press-surface 115. See e.g., FIG. 1A, FIG. 1B, FIG. 1C, and FIG. 1D. In some embodiments, second-press 113 may comprise a second-non-press-surface 117. See e.g., FIG. 1B, FIG. 1C, and FIG. 1F. In some embodiments, second-press-surface 115 may be disposed opposite of second-non-press-surface 117. In some embodiments, second-press-surface 115 and/or second-non-press-surface 117 may be major surface(s) of second-press 113 (e.g., as measured by surface area of second-press 113). In some embodiments, at least portions of second-press-surface 115 may removably contact the different makeup. In some embodiments, handle 103 may attach to second-press 113 at at least one location of second-non-press-surface 117, see e.g., FIG. 1B, FIG. 1C, and FIG. 1F. This at least one location of attachment may be about a geometric center of second-non-press-surface 117.

In some embodiments, second-press-surface 115 may be one or more of substantially: electrostatically neutral, smooth, flat, planar, rigid, semi-rigid, textured, combinations thereof, and/or the like. See e.g., FIG. 1A, FIG. 1B, FIG. 1C, and FIG. 1D. Having a smooth, flat, planar, rigid, and/or semi-rigid characteristic of second-press-surface 115 may promote pressing of the different makeup (such as against broken-makeup 507 within the different sized makeup pan 503). Having an electrostatically neutral second-press-surface 115, may minimize such makeup "sticking" to second-press-surface 115 due to opposite electrical charges, as may otherwise occur in static electricity environments. In some embodiments, second-press-surface 115 or second-press 113 may be manufactured from a substantially electrostatically neutral material.

In some embodiments, second-press 113 may be defined and bound by a second-closed-perimeter 119. See e.g., FIG. 1A, FIG. 1B, FIG. 1C, FIG. 1D, and FIG. 1F. In some embodiments, this second-closed-perimeter 119 may be substantially circular. In some embodiments, this second-closed-perimeter 119 may be substantially shaped as: a circle, a polygon, a parallelogram, a rectangle, a square; and/or the like. In some embodiments, this second-closed-perimeter 119 may be substantially shaped and sized to fit within the different sized makeup pan 503 that maybe holding the different makeup (such as holding different broken-makeup 503). A shape and size of a given makeup pan 503, including the different sized makeup pan 503, is predetermined. In some embodiments, this different sized makeup pan 503 may have an opening shaped substantially as: a circle, an oval, a polygon, a parallelogram, a rectangle, a square, an irregular polygon, a polygon with rounded corners, a star shape, and/or the like. See e.g., FIG. 5A through FIG. 5E which may show a circular shaped opening to a makeup pan 503. In some embodiments, the different sized makeup pan 503 may be smaller than the makeup pan 503 shown in FIG. 5A through FIG. 5E.

In some embodiments, first-press 101 may comprise a dimension-of-first-press 121. See e.g., FIG. 1D. For example, and without limiting the scope of the present invention, when closed-perimeter 109 may be substantially circular shaped or a circle, dimension-of-first-press 121 may be a diameter of closed-perimeter 109. In some embodiments, second-press 113 may comprise a dimension-of-second-press 123. See e.g., FIG. 1D. For example, and without limiting the scope of the present invention, when second closed-perimeter 119 may be substantially circular shaped or a circle, dimension-of-second-press 123 may be a diameter of second-closed-perimeter 119. In some embodiments, dimension-of-first-press 121 may be larger than dimension-of-second-press 123. In some embodiments, a ratio of dimension-of-first-press 121 to dimension-of-second-press 123 may be substantially 2.75. In some embodiments, a ratio of dimension-of-first-press 121 to dimension-of-second-press 123 may be substantially from 2.50 to 3.00.

In some embodiments, makeup-repair-tool 100 may comprise handle 103, first-press 101, and second-press 113. In some embodiments, handle 103 may be a structural elongate member with two opposing terminal ends. In some embodiments, each respective terminal end may be attached to a given press, such as first-press 101 and second-press 113, respectively. In some embodiments, longitude of handle 103 may be substantially orthogonal with respect to major surfaces of both first-press 101 (e.g., first-press-surface 105 and/or first-non-press-surface 107) and of second-press 113 (e.g., second-press-surface 115 and/or second-non-press-surface 117). In some embodiments, handle 103, first-press 101, and second-press 113 may be as described above and as shown in FIG. 1A, FIG. 1B, FIG. 1C, FIG. 1D, FIG. 1E, and FIG. 1F.

In some embodiments, makeup-repair-tool 100 may comprise handle 103, first-press 101, and second-press 113. In some embodiments, handle 103 may be integral with both first-press 101 and with second-press 113. In some embodiments, makeup-repair-tool 100 with handle 103, first-press 101, and second-press 113 may be manufactured as a single integral article of manufacture. For example, and without limiting the scope of the present invention, makeup-repair-tool 100 may be substantially manufactured via injection molding, 3D printing, and/or the like.

In some embodiments, the various presses, such as first-press 101 and second-press 113 may be substantially disc shaped. In some embodiments, the various presses, such as first-press 101 and second-press 113 may be substantially circular disc shapes. See e.g., FIG. 1A, FIG. 1B, FIG. 1C, FIG. 1D, FIG. 1E, and FIG. 1F.

Figure 2A:
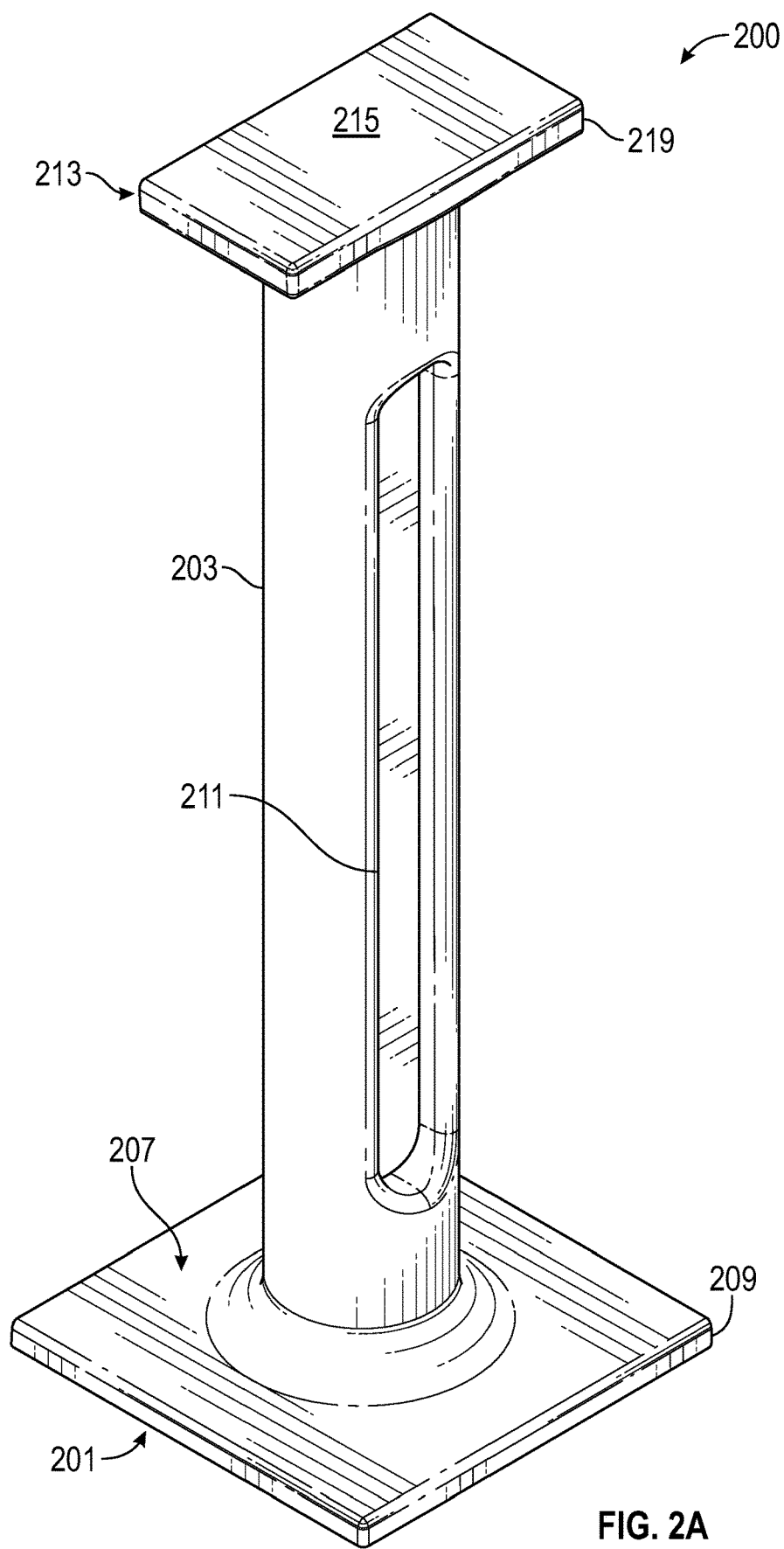
FIG. 2A may depict a top perspective view of a makeup-repair-tool according to a second embodiment.
Figure 2B:
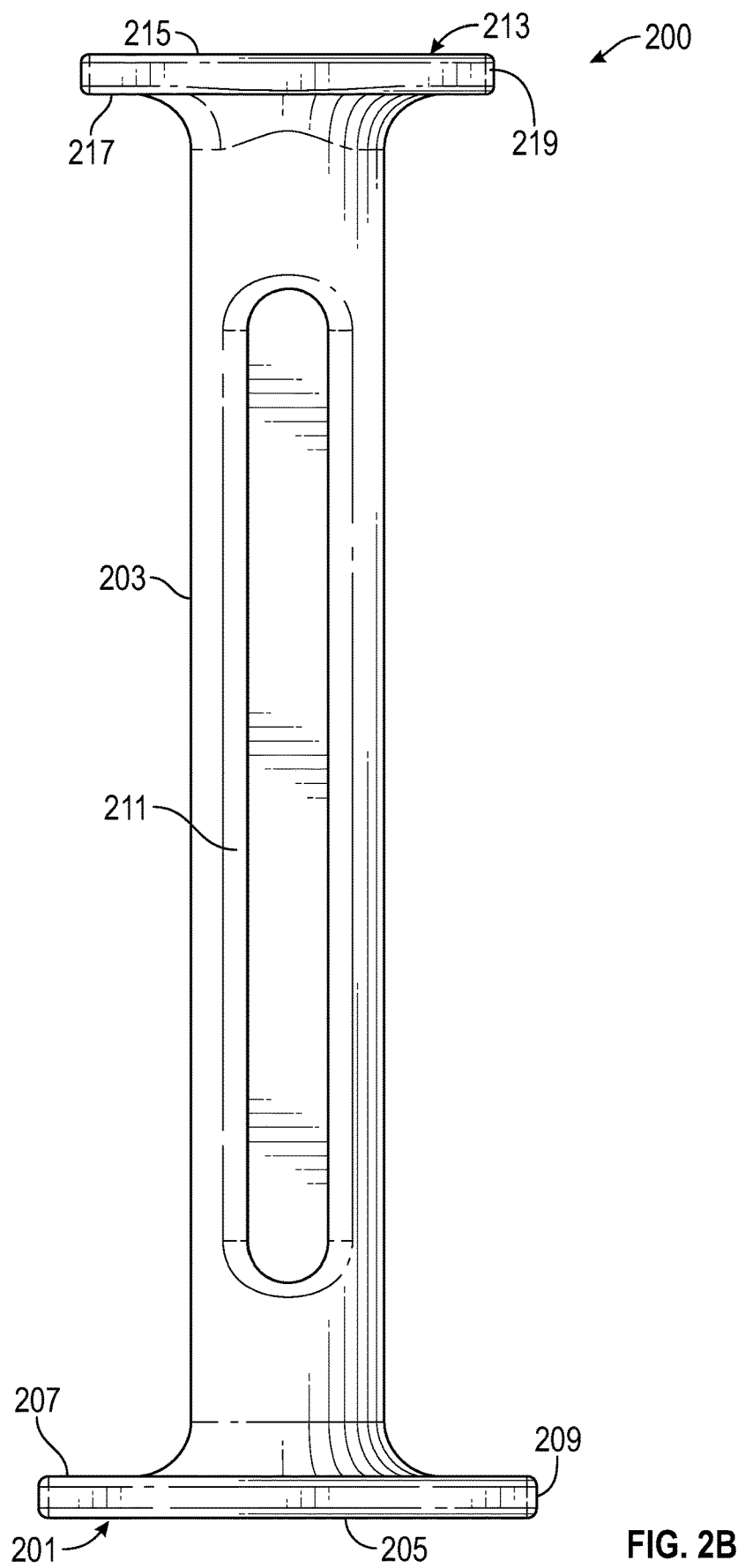
FIG. 2B may depict a front view and/or a back view of the makeup-repair-tool of FIG. 2A.
Figure 2C:
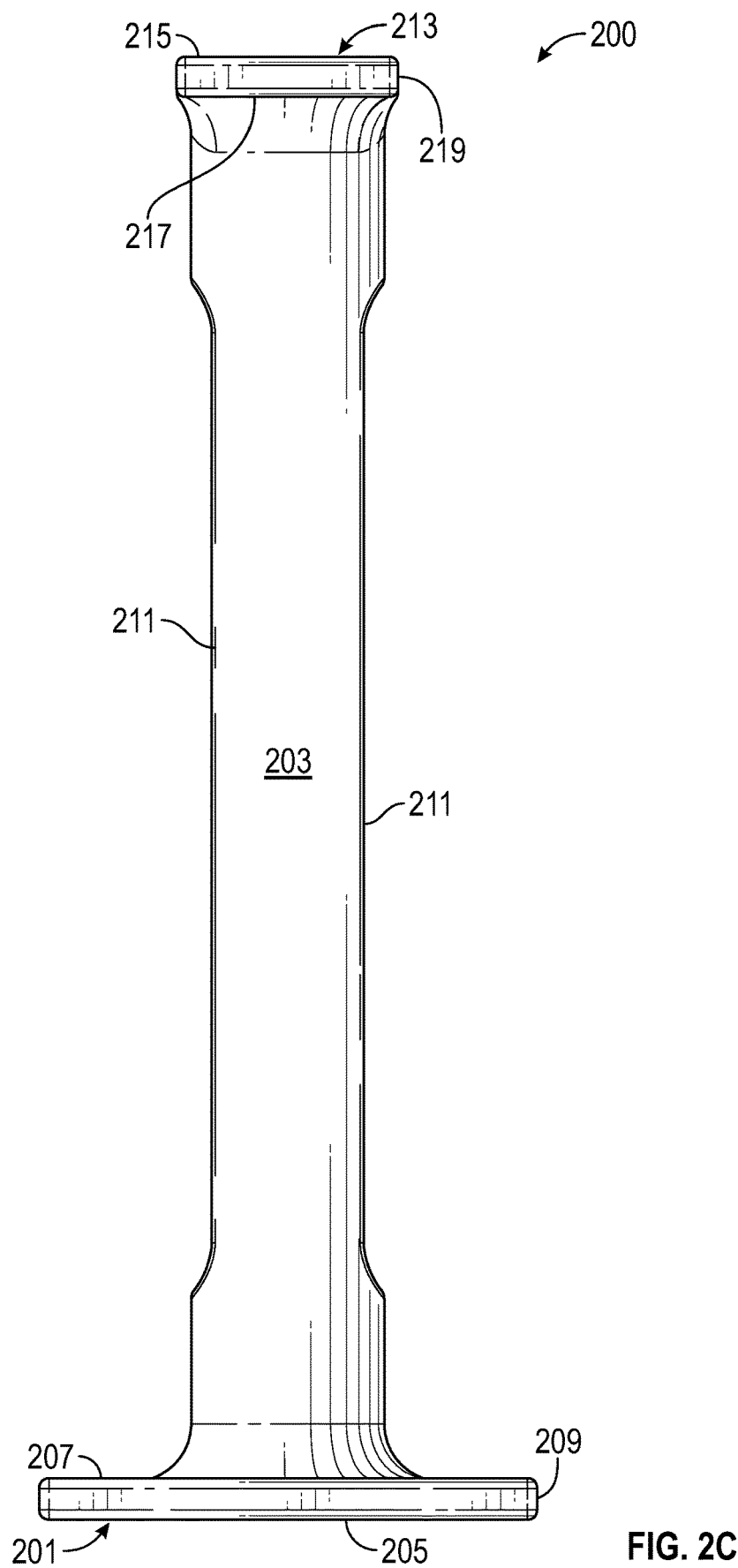
FIG. 2C may depict a left-side view and/or a right-side view of the makeup-repair-tool of FIG. 2A.
Figure 2D:
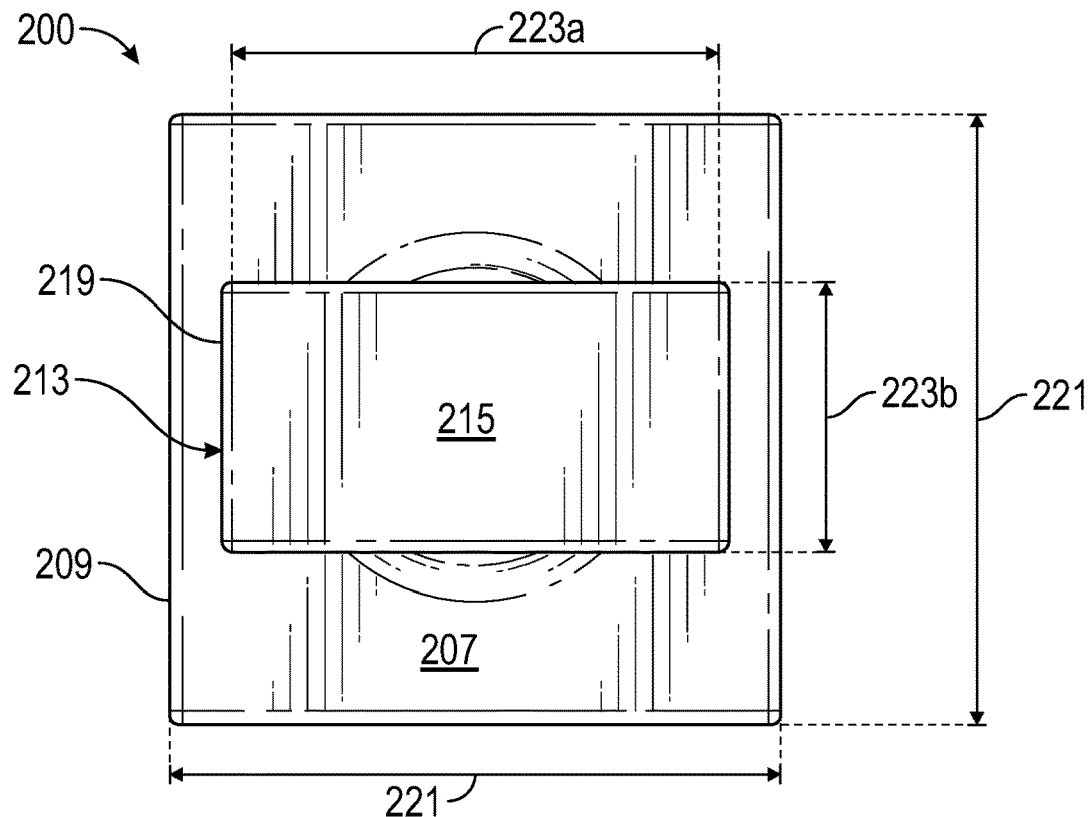
FIG. 2D may depict a top view of the makeup-repair-tool of FIG. 2A.
Figure 2E:
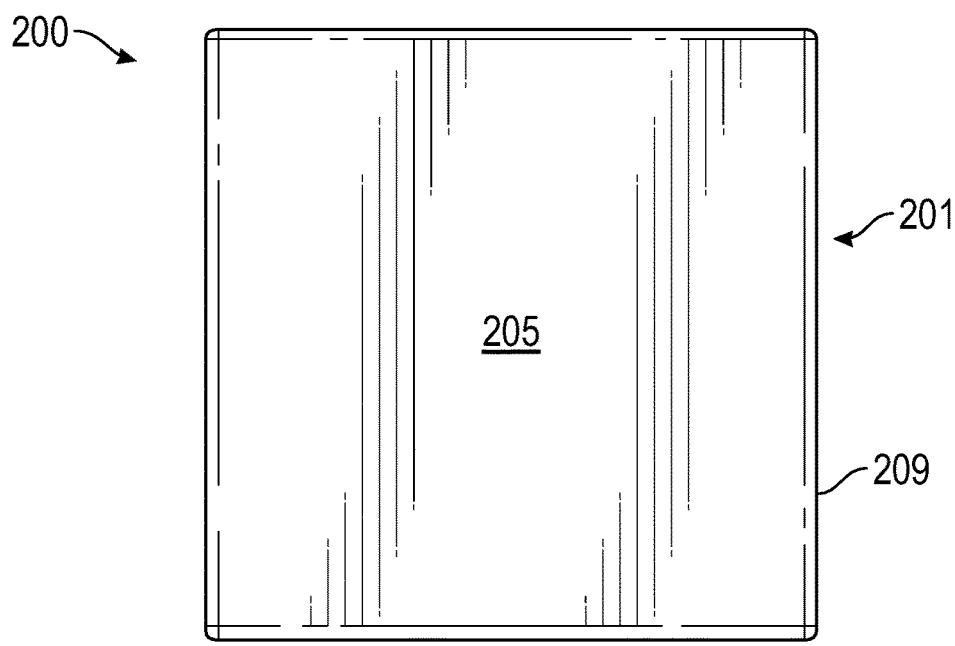
FIG. 2E may depict a bottom view of the makeup-repair-tool of FIG. 2A.
Figure 2F:
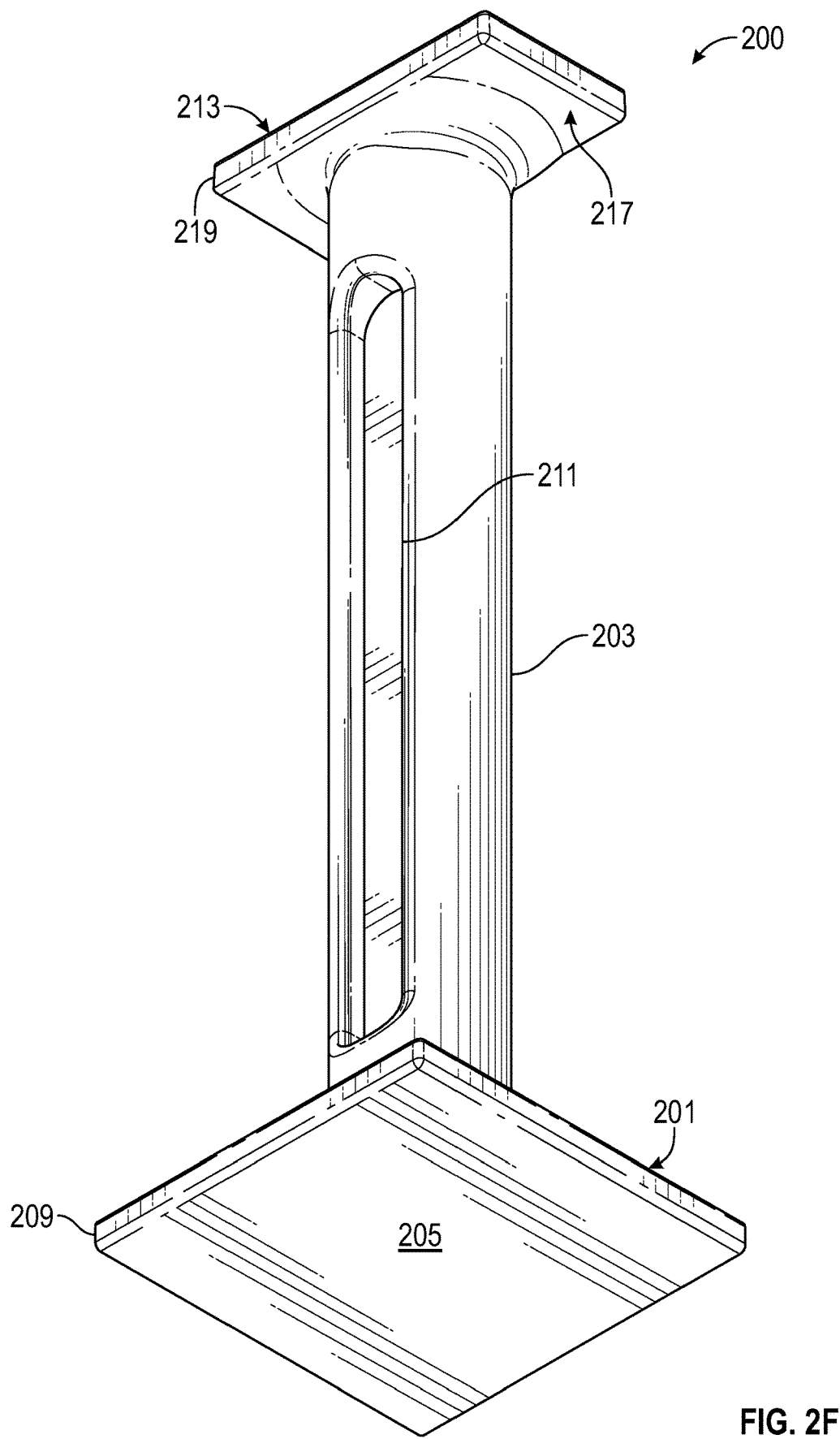
FIG. 2F may depict a bottom perspective view of the makeup-repair-tool of FIG. 2A.

FIG. 2A may depict a top perspective view of a makeup-repair-tool 200 according to a second embodiment. FIG. 2B may depict a front view and/or a back view of makeup-repair-tool 200. In some embodiments, the front view and the back view may be substantially similar or substantially identical. FIG. 2C may depict a left-side view and/or a right-side view of makeup-repair-tool 200. In some embodiments, the left-side view and the right-side view may be substantially similar or substantially identical. FIG. 2D may depict a top view of makeup-repair-tool 200. FIG. 2E may depict a bottom view of makeup-repair-tool 200. FIG. 2F may depict a bottom perspective view of makeup-repair-tool 200.

Discussing FIG. 2A, FIG. 2B, FIG. 2C, and FIG. 2F, in some embodiments, makeup-repair-tool 200 may comprise a first-press 201 and a handle 203. In some embodiments, first-press 201 may be for pressing against makeup to compact and level the makeup. See e.g., FIG. 5E for an example of such a use; although in FIG. 5E it may be makeup-repair-tool 100 that may be shown in use; note, it is expressly contemplated that makeup-repair-tool 100 shown in FIG. 5E may be replaced with makeup-repair-tool 200 without deviating from the scope of embodiments of this invention. In some embodiments, this makeup may be broken-makeup 507. Continuing discussing FIG. 2A, FIG. 2B, FIG. 2C, and FIG. 2F, in some embodiments, handle 203 may be attached to first-press 201. In some embodiments, when a force may be removably exerted upon handle 203, then first-press 201 may press against the makeup (e.g., against the broken-makeup 507). In some embodiments, when a force may be removably exerted upon handle 203, then first-press 201 may press against broken-makeup 507 to level and compact it, as may be illustrated in FIG. 5E.

In some embodiments, first-press 201 may comprise a first-press-surface 205 (see e.g., FIG. 2B, FIG. 2C, FIG. 2E, and FIG. 2F). In some embodiments, first-press 201 may comprise a first-non-press-surface 207 (see e.g., FIG. 2A, FIG. 2B, FIG. 2C, and FIG. 2D). In some embodiments, first-press-surface 205 may be disposed opposite of first-non-press-surface 207. In some embodiments, first-press-surface 205 and/or first-non-press-surface 207 may be major surface(s) of first-press 201 (e.g., as measured by surface area of first-press 201). In some embodiments, at least portions of first-press-surface 205 may removably contact the makeup (e.g., the broken-makeup 507). In some embodiments, handle 203 may attach to first-press 201 at at least one location of first-non-press-surface 207, see e.g., FIG. 2A, FIG. 2B, and FIG. 2C. This at least one location of attachment may be about a geometric center of first-non-press-surface 207.

In some embodiments, first-press-surface 205 may be one or more of substantially: electrostatically neutral, smooth, flat, planar, rigid, semi-rigid, textured, combinations thereof, and/or the like. See e.g., FIG. 2B, FIG. 2C, FIG. 2E, and FIG. 2F. Having a smooth, flat, planar, rigid, and/or semi-rigid characteristic of first-press-surface 205 may promote pressing and compacting of the makeup (such as against broken-makeup 507). Having an electrostatically neutral first-press-surface 205, may minimize such makeup "sticking" to first-press-surface 205 due to opposite electrical charges, as may otherwise occur in static electricity environments. In some embodiments, first-press-surface 205 or first-press 201 may be manufactured from a substantially electrostatically neutral material.

In some embodiments, first-press 201 may be defined and bound by a closed-perimeter 209. See e.g., FIG. 2A, FIG. 2B, FIG. 2C, FIG. 2D, FIG. 2E, and FIG. 2F. In some embodiments, this closed-perimeter 209 may be substantially circular. In some embodiments, this closed-perimeter 209 may be substantially shaped as: a circle, a polygon, a parallelogram, a rectangle, a square; and/or the like. In some embodiments, this closed-perimeter 209 may be substantially shaped and sized to fit within a makeup pan 503 that may be holding the makeup (such as holding the broken-makeup 503). A shape and size of a given makeup pan 503 is predetermined and fixed. In some embodiments, the makeup pan 503 may have an opening shaped substantially as: a circle, an oval, a polygon, a parallelogram, a rectangle, a square, an irregular polygon, a polygon with rounded corners, a star shape, and/or the like. See e.g., FIG. 5A through FIG. 5E which may show a circular shaped opening to makeup pan 503. Note it is expressly contemplated that circular shaped makeup pan 503 shown in FIG. 5A through FIG. 5E may be replaced with a makeup pan 503 that is substantially shaped as a polygon, a parallelogram, a rectangle, a square, an irregular polygon, a polygon with rounded corners, a star shape, and/or the like; such that the shape of closed-perimeter 209 may fit concentrically within the shape of makeup pan 503.

In some embodiments, handle 203 may be one or more of substantially: an elongate member, a structural member, a rigid member, a semi-rigid member, a straight member, combinations thereof, and/or the like. See e.g., FIG. 2A, FIG. 2B, FIG. 2C, and FIG. 2F. In some embodiments, handle 203 may be an elongate member that may extend substantially orthogonally from a major surface of first-press 201. See e.g., FIG. 2A, FIG. 2B, and FIG. 2C. In some embodiments, such a major surface may be first-non-press-surface 207. In some embodiments, handle 203 may be substantially similar to handle 103 in structure, function, or both structure and function.

In some embodiments, handle 203 may be an elongate member that may comprise at least one slot 211. In some embodiments, at least one slot 211 may run along at least some of a length of handle 203. In some embodiments, at least one slot 211 may have a longitude that may be substantially parallel with a longitude of the elongate member of handle 203. See e.g., FIG. 2A, FIG. 2B, FIG. 2C, and FIG. 2F.

In some embodiments, handle 203 may be an elongate member that may comprise two opposing slots 211. In some embodiments, these two opposing slots 211 may run along at least some of a length of handle 203. In some embodiments, these two opposing slots 211 each may have a longitude that may be substantially parallel with a longitude of the elongate member of handle 203. See e.g., FIG. 2A, FIG. 2B, FIG. 2C, and FIG. 2F.

In some embodiments, slot(s) 211 may reduce material costs in manufacturing a given handle 203 because such slot(s) 211 allow for void space. In some embodiments, slot(s) 211 may function as structural ribs or girders for a given handle 203, providing increased rigidity to handle 203 that otherwise would be absent in a handle without such slot(s) 211. In some embodiments, slot(s) 211 may function to reduce shrinkage problems from cooling post injection molding of a given handle 203 that otherwise would be absent in a handle without such slot(s) 211.

In some embodiments, makeup-repair-tool 200 may comprise a second-press 213. In some embodiments, second-press 213 may be attached to handle 203. In some embodiments, second-press 213 may be for pressing against different makeup; i.e., makeup within a different sized makeup pan 503 as compared against a makeup pan 503 that receives first-press 201. In some embodiments, when a different force may be removably exerted upon handle 103, then second-press 213 may press against the different makeup within the different sized makeup pan 503. See e.g., FIG. 2A, FIG. 2B, FIG. 2C, FIG. 2D, and FIG. 2F.

In some embodiments, second-press 213 may comprise a second-press-surface 215. See e.g., FIG. 2A, FIG. 2B, FIG. 2C, and FIG. 2D. In some embodiments, second-press 213 may comprise a second-non-press-surface 217. See e.g., FIG. 2B, FIG. 2C, and FIG. 2F. In some embodiments, second-press-surface 215 may be disposed opposite of second-non-press-surface 217. In some embodiments, second-press-surface 215 and/or second-non-press-surface 217 may be major surface(s) of second-press 213 (e.g., as measured by surface area of second-press 213). In some embodiments, at least portions of second-press-surface 215 may removably contact the different makeup. In some embodiments, handle 203 may attach to second-press 213 at at least one location of second-non-press-surface 217, see e.g., FIG. 2B, FIG. 2C, and FIG. 2F. This at least one location of attachment may be about a geometric center of second-non-press-surface 217.

In some embodiments, second-press-surface 215 may be one or more of substantially: electrostatically neutral, smooth, flat, planar, rigid, semi-rigid, textured, combinations thereof, and/or the like. See e.g., FIG. 2A, FIG. 2B, FIG. 2C, and FIG. 2D. Having a smooth, flat, planar, rigid, and/or semi-rigid characteristic of second-press-surface 215 may promote pressing of the different makeup (such as against broken-makeup 507 within the different sized makeup pan 503). Having an electrostatically neutral second-press-surface 215, may minimize such makeup "sticking" to second-press-surface 215 due to opposite electrical charges, as may otherwise occur in static electricity environments. In some embodiments, second-press-surface 215 or second-press 213 may be manufactured from a substantially electrostatically neutral material.

In some embodiments, second-press 213 may be defined and bound by a second-closed-perimeter 219. See e.g., FIG. 2A, FIG. 2B, FIG. 2C, FIG. 2D, and FIG. 2F. In some embodiments, this second-closed-perimeter 219 may be substantially circular. In some embodiments, this second-closed-perimeter 219 may be substantially shaped as: a circle, a polygon, a parallelogram, a rectangle, a square; and/or the like. In some embodiments, this second-closed-perimeter 219 may be substantially shaped and sized to fit within the different sized makeup pan 503 that maybe holding the different makeup (such as holding different broken-makeup 503). A shape and size of a given makeup pan 503, including the different sized makeup pan 503, is predetermined. In some embodiments, this different sized makeup pan 503 may have an opening shaped substantially as: a circle, an oval, a polygon, a parallelogram, a rectangle, a square, an irregular polygon, a polygon with rounded corners, a star shape, and/or the like. See e.g., FIG. 5A through FIG. 5E which may show a circular shaped opening to a makeup pan 503. In some embodiments, the different sized makeup pan 503 may be smaller than the makeup pan 503 shown in FIG. 5A through FIG. 5E.

In some embodiments, first-press 201 may comprise a dimension-of-first-press 221. See e.g., FIG. 2D. For example, and without limiting the scope of the present invention, when closed-perimeter 209 may be substantially square shaped or squarish, dimension-of-first-press 221 may be may correspond to a length of a side of closed-perimeter 209. In some embodiments, second-press 213 may comprise a dimension-of-second-press 223a. See e.g., FIG. 2D. For example, and without limiting the scope of the present invention, when second closed-perimeter 219 may be substantially as a parallelogram or a rectangle, dimension-of-second-press 223a may be a longer length of a longer side of second-closed-perimeter 219. In some embodiments, second-press 213 may comprise a dimension-of-second-press 223b. See e.g., FIG. 2D. For example, and without limiting the scope of the present invention, when second closed-perimeter 219 may be substantially as a parallelogram or a rectangle, dimension-of-second-press 223b may be a shorter length (e.g., a width) of a shorter side of second-closed-perimeter 219. In some embodiments, dimension-of-first-press 221 may be larger (longer) than dimension-of-second-press 223a. In some embodiments, dimension-of-first-press 221 may be larger (longer) than dimension-of-second-press 223b. In some embodiments, dimension-of-second-press 223a may be larger (longer) than dimension-of-second-press 223b. In some embodiments, a ratio of dimension-of-first-press 221 to dimension-of-second-press 223a may be substantially 1.22. In some embodiments, a ratio of dimension-of-first-press 221 to dimension-of-second-press 223a may be substantially from 0.95 to 1.55. In some embodiments, a ratio of dimension-of-first-press 221 to dimension-of-second-press 223b may be substantially 2.32. In some embodiments, a ratio of dimension-of-first-press 221 to dimension-of-second-press 223b may be substantially from 2.00 to 2.55.

In some embodiments, makeup-repair-tool 200 may comprise handle 203, first-press 201, and second-press 213. In some embodiments, handle 203 may be a structural elongate member with two opposing terminal ends. In some embodiments, each respective terminal end may be attached to a given press, such as first-press 201 and second-press 213, respectively. In some embodiments, longitude of handle 203 may be substantially orthogonal with respect to major surfaces of both first-press 201 (e.g., first-press-surface 205 and/or first-non-press-surface 207) and of second-press 213 (e.g., second-press-surface 215 and/or second-non-press-surface 217). In some embodiments, handle 203, first-press 201, and second-press 213 may be as described above and as shown in FIG. 2A, FIG. 2B, FIG. 2C, FIG. 2D, FIG. 2E, and FIG. 2F.

In some embodiments, makeup-repair-tool 200 may comprise handle 203, first-press 201, and second-press 213. In some embodiments, handle 203 may be integral with both first-press 201 and with second-press 213. In some embodiments, makeup-repair-tool 200 with handle 203, first-press 201, and second-press 213 may be manufactured as a single integral article of manufacture. For example, and without limiting the scope of the present invention, makeup-repair-tool 200 may be substantially manufactured via injection molding, 3D printing, and/or the like.

In some embodiments, the various presses, such as first-press 201 and second-press 213 may be substantially shaped as flattened rectangular prisms. See e.g., FIG. 2A, FIG. 2B, FIG. 2C, FIG. 2D, FIG. 2E, and FIG. 2F.

Figure 3:
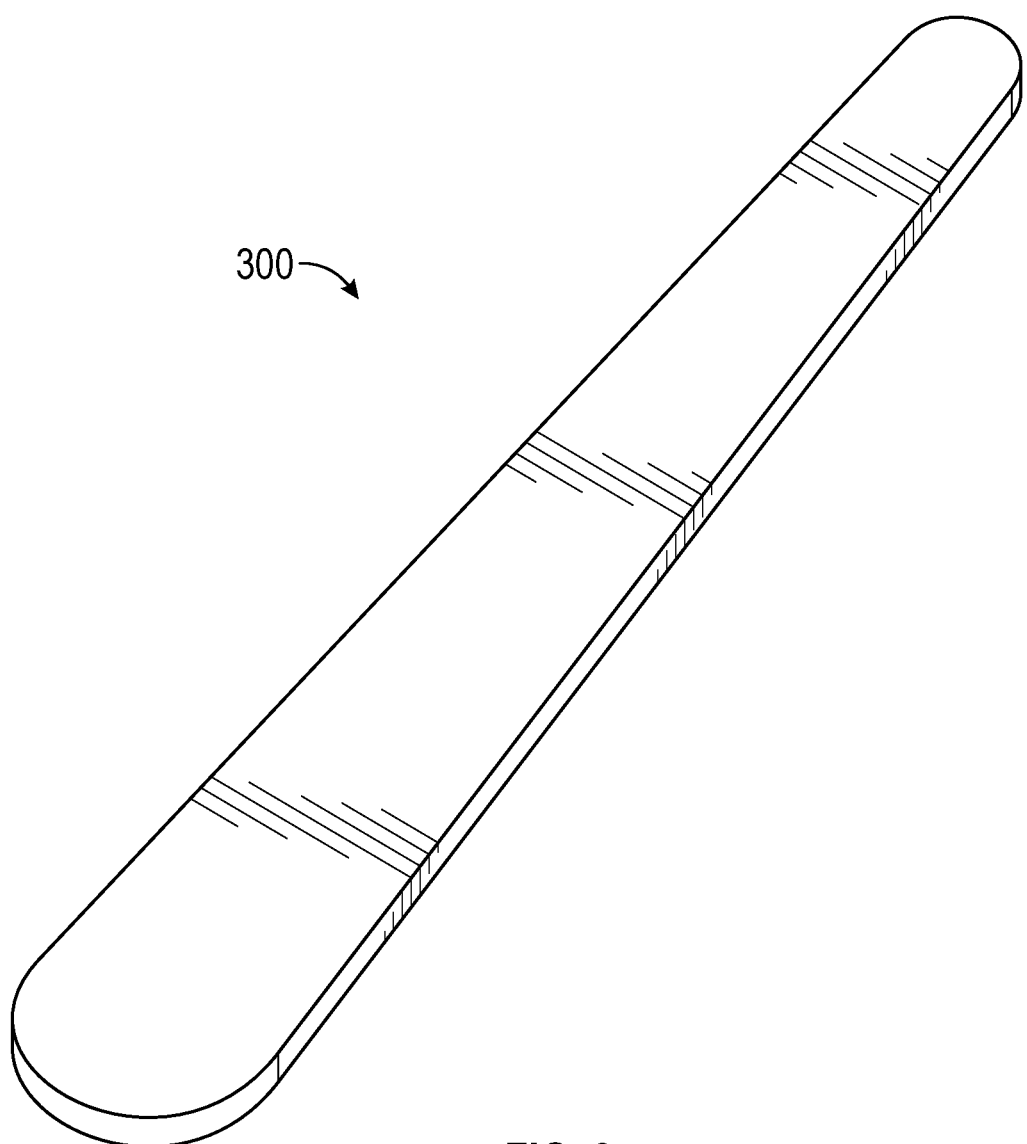
FIG. 3 may depict a perspective view of a spatula.

FIG. 3 may depict a perspective view of a spatula 300. In some embodiments, spatula 300 may be used for scraping and/or returning broken-makeup 507 (e.g., such as fragment-of-makeup 505) that may fallen out of makeup pan 503 back into makeup pan 503. In some embodiments, spatula 300 may be used for smoothing out broken-makeup 507, prior to such broken-makeup 507 being removably pressed with a given makeup-repair-tool 100 or 200.

In some embodiments, spatula 300 may be one or more of substantially: electrostatically neutral, smooth, flat, planar, rigid, semi-rigid, textured, straight, a planar elongate member, a flattened elongate member, a structural member, combinations thereof, and/or the like. See e.g., FIG. 3, FIG. 5A, FIG. 5C, and FIG. 5D. In some embodiments, having a smooth, flat, planar, rigid, and/or semi-rigid characteristic of spatula 300 may promote gathering and/or scraping of fragment-of-makeup 505 back into makeup pan 503. See e.g., FIG. 5A. In some embodiments, having a smooth, flat, planar, rigid, and/or semi-rigid characteristic of spatula 300 may assist with testing a consistency of broken-makeup 507. See e.g., FIG. 5C. In some embodiments, having a smooth, flat, planar, rigid, and/or semi-rigid characteristic of spatula 300 may assist with smoothing broken-makeup 507. See e.g., FIG. 5D. In some embodiments, having an electrostatically neutral spatula 300, may minimize such makeup "sticking" to spatula 300 due to opposite electrical charges, as may otherwise occur in static electricity environments. In some embodiments, spatula 300 may be manufactured from a substantially electrostatically neutral material.

Figure 4A:
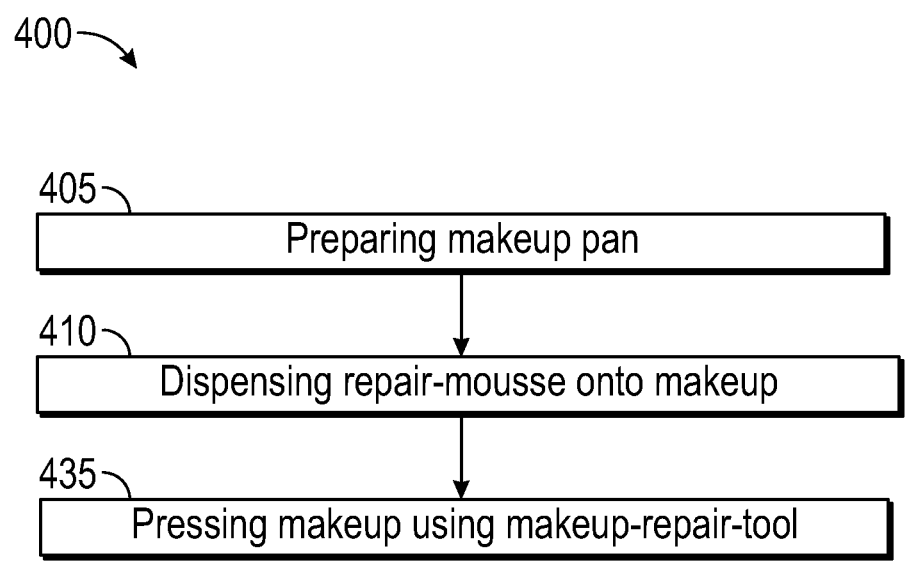
FIG. 4A may depict steps in a method for repairing makeup.

FIG. 4A may depict steps in a method 400 for repairing makeup. In some embodiments, method 400 may comprise the steps of: step 405, step 410, and step 435. In some embodiments, step 410 may follow step 405. See e.g., FIG. 4A. In some embodiments, step 435 may follow step 410 (although not always directly, i.e., in some embodiments, other steps may be disposed between step 410 and step 435). In some embodiments, method 400 may begin at step 410.

In some embodiments, step 405 may be a step of preparing makeup pan 503 to receive at least some broken makeup 507. In some embodiments, step 405 may entail using spatula 300 to scrape and/or gather fragment-of-makeup 505 residing outside of makeup pan 503 back into makeup pan 503. See e.g., FIG. 4A and FIG. 5A.

In some embodiments, step 410 may be a step of dispensing at least some repair-mousse 513 onto the at least some broken makeup 507 (that in some embodiments, may be located within the makeup pan 503). In some embodiments, step 410 may entail covering broken-makeup 507 (within makeup pan 503) with repair-mousse 513. In some embodiments, step 410 may entail "wetting" broken-makeup 507 (within makeup pan 503) with repair-mousse 513. See e.g., FIG. 4A and FIG. 5B.

In some embodiments, step 435 may be a step of pressing the at least some broken makeup 507 within the makeup pan 503 using makeup-repair-tool 100 (or 200). Makeup-repair-tool 100 or 200 should be selected to match a size and shape of the given makeup pan 503. In some embodiments, the broken-makeup 507 to be pressed with makeup-repair-tool 100 or 200 in step 435 may have already been treated with makeup-mousse 513 in step 410. See e.g., FIG. 4A and FIG. 5E. In some embodiments, step 435 may be a final step in method 400.

Figure 4B:
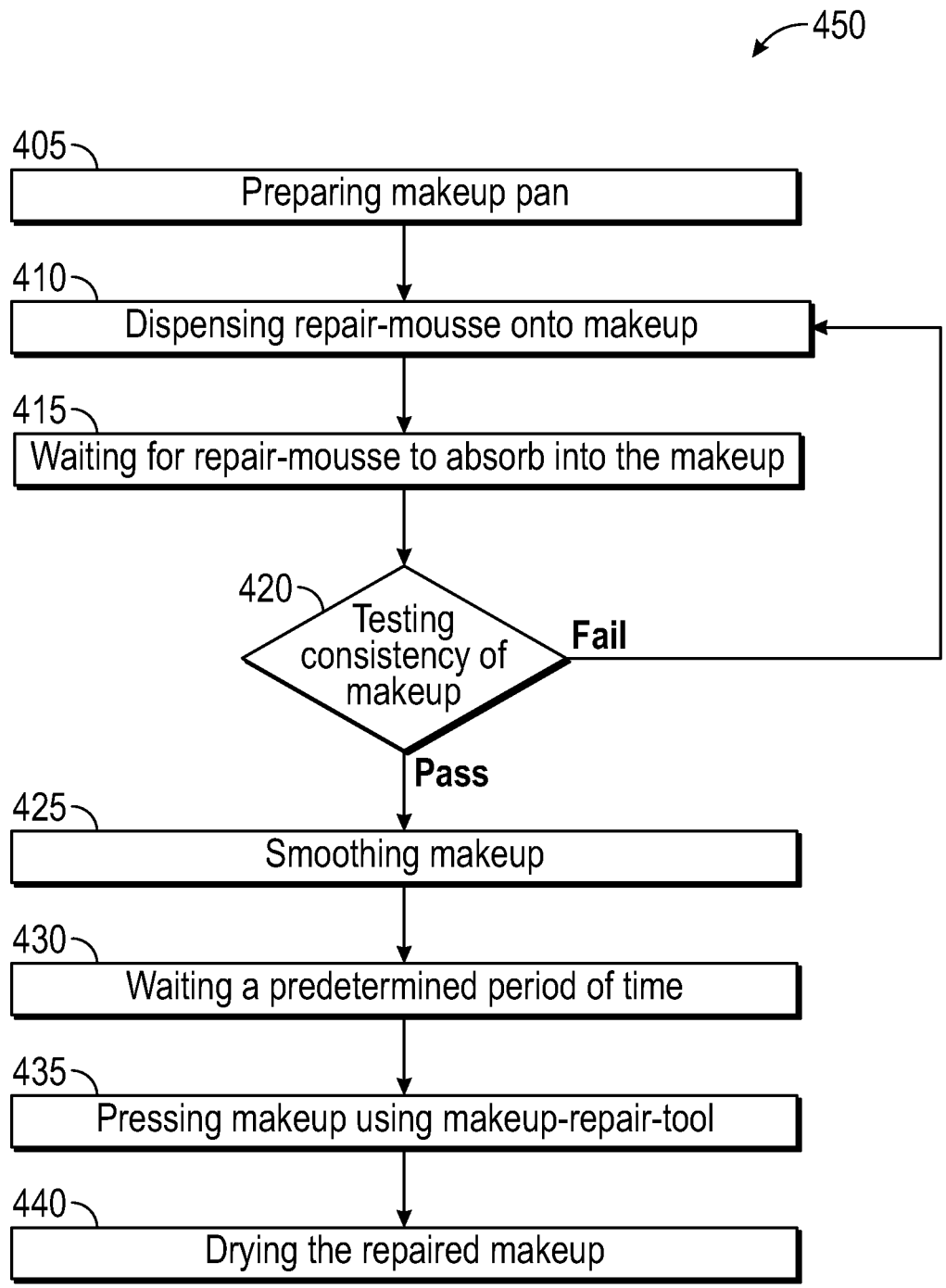
FIG. 4B may depict steps in a method for repairing makeup.

FIG. 4B may depict steps of method 450 for repairing makeup. Method 450 may provide for some additional steps as compared against method 400. In some embodiments, method 450 may comprise steps 405 and 410 as noted above. In some embodiments, method 450 may further comprise step 415. In some embodiments, step 415 may follow step 410. In some embodiments, step 415 may be a step of waiting for repair-mousse 513 has adsorbed into the broken-makeup 507. In some embodiments, this waiting time period may predetermined. In some embodiments, this waiting time period may be about sixty to thirty seconds. In some embodiments, this waiting time period may be one minute or less. In some embodiments, this waiting time period may be two minutes or less. In some embodiments, this waiting time period may be three minutes or less. In some embodiments, this waiting time period may be five minutes or less. In some embodiments, this waiting time period may be ten minutes or less. In some embodiments, this waiting time period may be fifteen minutes or less. In some embodiments, this waiting time period may be determined from observing repair-mousse 513 has visually wetted the broken-makeup 507 or has visually been adsorbed into the broken-makeup 507. See e.g., FIG. 4B.

Continuing discussing FIG. 4B, in some embodiments, method 450 may further comprise step 420. In some embodiments, step 420 may follow step 415. In some embodiments, step 420 may be a step of testing a consistency of broken-makeup 507, after such broken-makeup 507 has been treated with repair-mousse 513. In some embodiments, if such a consistency is appropriate (i.e., at least a predetermined consistency), then method 450 may progress to step 425; whereas, if the consistency is inappropriate (i.e., not the at least a predetermined consistency), then method 450 may cycle back to step 410. In some embodiments, the at least a predetermined consistency may be one or more of: paste-like, malleable, non-sticky, combinations thereof, and/or the like. In some embodiments, testing consistency of broken-makeup 507 in step 420 may be tested with spatula 300, by dragging spatula 300 across broken-makeup 507 and observing the broken-makeup 507 to see if broken-makeup 507 may be paste-like, malleable, non-sticky, combinations thereof, and/or the like. See e.g., FIG. 4B and FIG. 5C.

Continuing discussing FIG. 4B, in some embodiments, method 450 may further comprise step 425. In some embodiments, step 425 may follow step 420 if broken-makeup 507 consistency was tested as appropriate. In some embodiments, step 425 may be a step of smoothing the broken-makeup 507. In some embodiments, step 425 may be carried out via using spatula 300 for the smoothing. See e.g., FIG. 4B and FIG. 5D.

Continuing discussing FIG. 4B, in some embodiments, method 450 may further comprise step 430. In some embodiments, step 430 may follow step 425. In some embodiments, step 430 may be a step of waiting a predetermined period of time, prior to continuing with step 435. In some embodiments, this predetermined period of time may be from twenty minutes to ten minutes. See e.g., FIG. 4B.

In some embodiment, step 430 may be omitted; and step 425 may progress into step 435.

Continuing discussing FIG. 4B, in some embodiments, method 450 may further comprise step 435. In some embodiments, step 435 may follow step 430 (or may follow step 425, in some embodiments). As noted above, in some embodiments, step 435 may be a step of pressing the at least some broken makeup 507 within the makeup pan 503 using makeup-repair-tool 100 (or 200). See e.g., FIG. 4B and FIG. 5E.

Continuing discussing FIG. 4B, in some embodiments, method 450 may further comprise step 440. In some embodiments, step 440 may follow step 435. In some embodiments, step 440 may be a step of drying the broken-makeup 507 that has now been repaired. In some embodiments, this drying may be natural air drying. In some embodiments, this drying may be sufficiently complete after ten hours, or after eight hours, or after six hours, or after four hours—depending upon local environmental conditions (e.g., temperature and humidity). In some embodiments, drying under step 440 may be carried with a lid of makeup container 501 open; so that the now repaired broken-makeup 507 may be exposed to environmental air for drying. In some embodiments, step 440 may be a final step of method 450. See e.g., FIG. 4B.

Figure 4C:
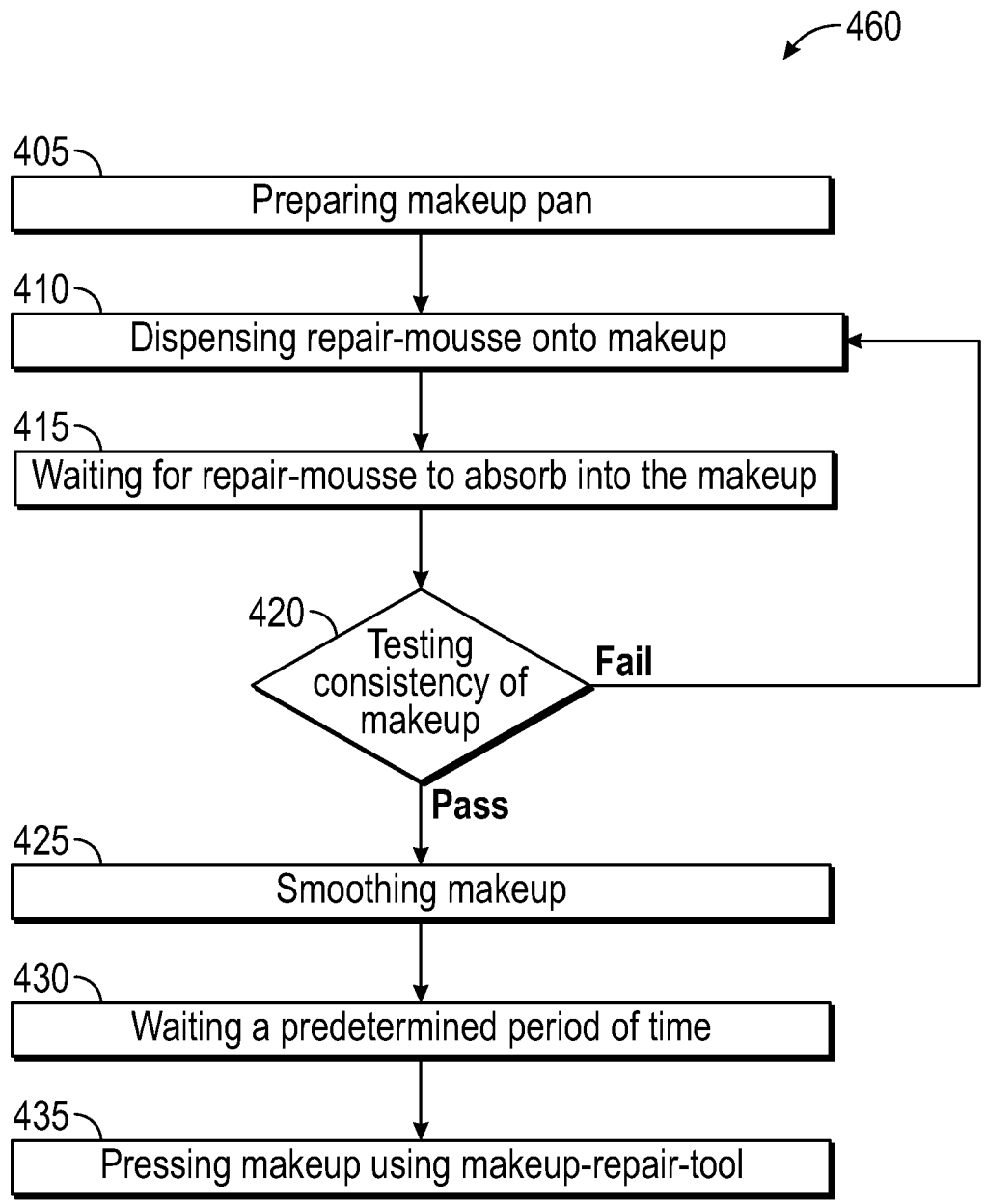
FIG. 4C may depict steps in a method for repairing makeup.

FIG. 4C may depict steps of method 460 for repairing makeup. Method 460 may be similar to method 450; except, in method 460 there may not be step 440.

In some embodiments, method 400, method 450 or method 460 may be methods for refreshing unbroken makeup, as opposed to methods for repairing broken-makeup 507. In some embodiments, in such methods of use, step 405 may be omitted; and the methods may begin with step 410.

Figure 5A:
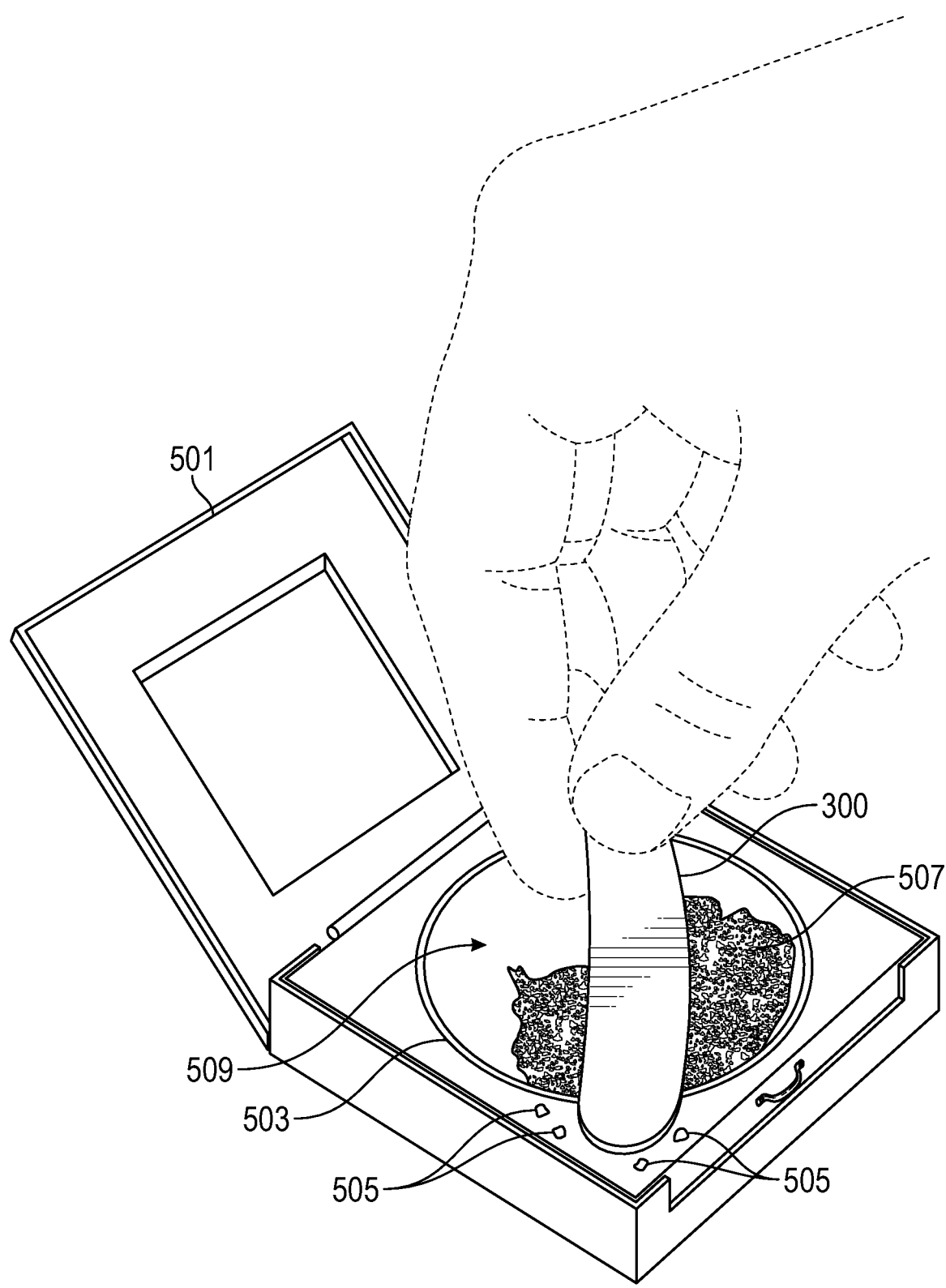
FIG. 5A may depict a spatula in use preparing a makeup pan for repairing broken makeup.

FIG. 5A may depict spatula 300 in use preparing a given makeup pan 503 for method 400 or method 450. FIG. 5A may depict an implementation of step 405. In FIG. 5A, spatula 300 may be in use to scrape and/or gather fragment-of-makeup 505, which may be type of broken-makeup 507 that has fallen out of makeup pan 503. Makeup pan 503 may be the pan portion of makeup container 501; wherein the pan portion holds the makeup (such as normal makeup 509 and/or broken-makeup 507). Normal makeup 509 may be unbroken makeup (or previously repaired broken-makeup 507). In some embodiments, makeup container 501 may be a makeup container for holding makeup in the makeup pan 503 of makeup container 501. Such makeup may be cosmetics. Such makeup may be selected from: powders, mineral based makeups, blush, foundation, bronzers, concealers, eyeliners, mascaras, creams, nail polish, and the like.

Figure 5B:
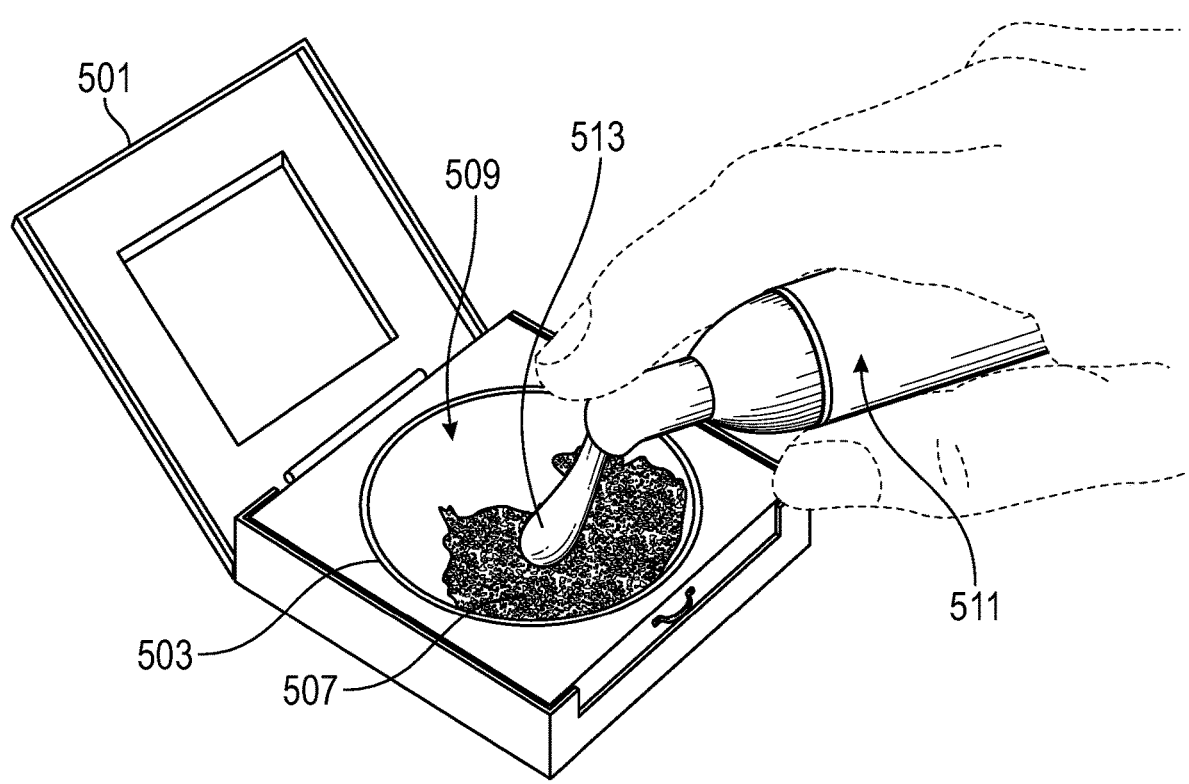
FIG. 5B may depict repair-mousse being dispenses onto broken makeup.

FIG. 5B may depict at least some repair-mousse 513 being dispensed onto broken-makeup 507. FIG. 5B may depict an implementation of step 410. In FIG. 5B, container 511 may be a container holding repair-mousse 513.

In some embodiments, repair-mousse 513 may also be known as one or more of: "liquid composition for reconstituting pressed powder cosmetics"; "composition for reconstituting loosened compact cosmetic powders"; "liquid composition for reconstituting loosened compact cosmetic powders"; and/or the like. In some embodiments, repair-mousse 513 may be discussed and disclosed in U.S. patent application Ser. No. 15/606,802 filed May 26, 2017.

Figure 5C:
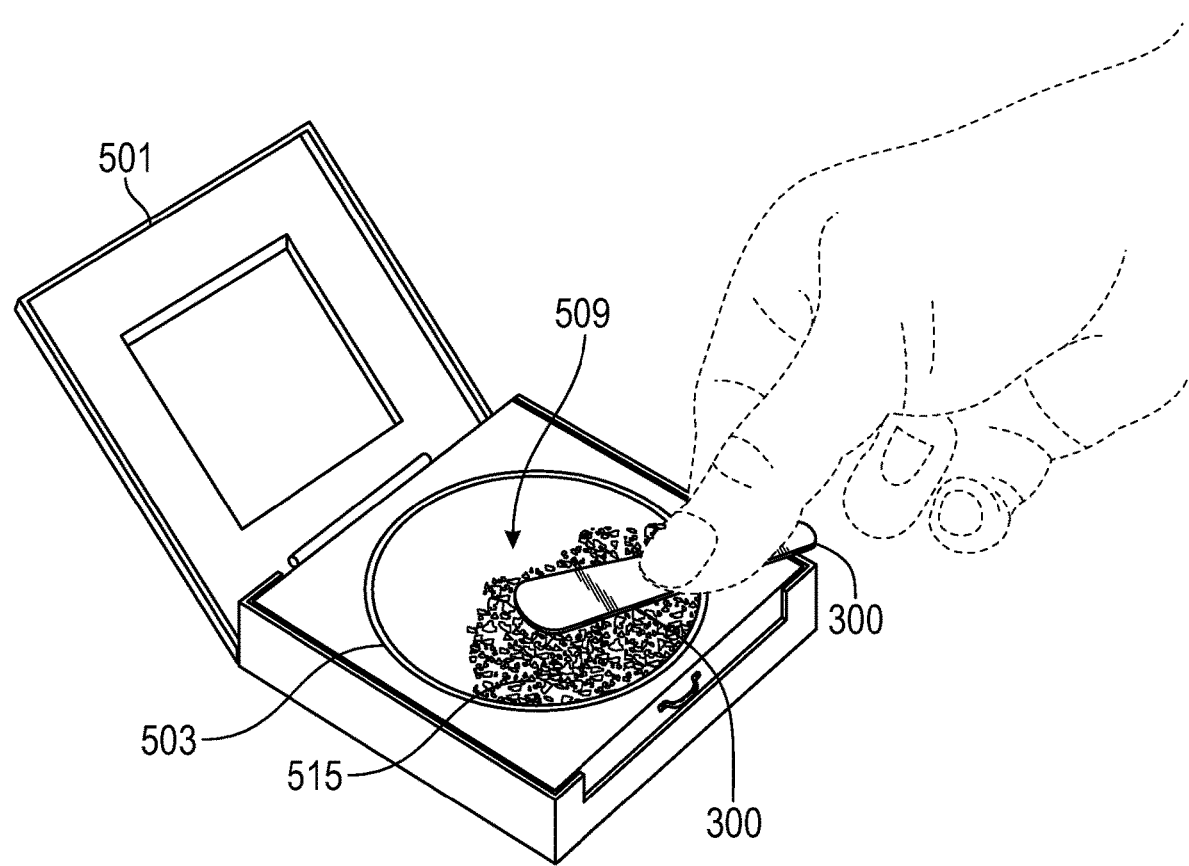
FIG. 5C may depict a spatula in use testing a consistency of the broken makeup that has adsorbed at least some of the dispensed repair-mousse.

FIG. 5C may depict spatula 300 in use testing a consistency of the broken-makeup 507 that may have adsorbed at least some of the dispensed repair-mousse 513. FIG. 5C may depict an implementation of step 420. FIG. 5C may show damp-makeup 515, which may be makeup (e.g., broken-makeup 507) that may have adsorbed at least some of the dispensed repair-mousse 513.

Figure 5D:
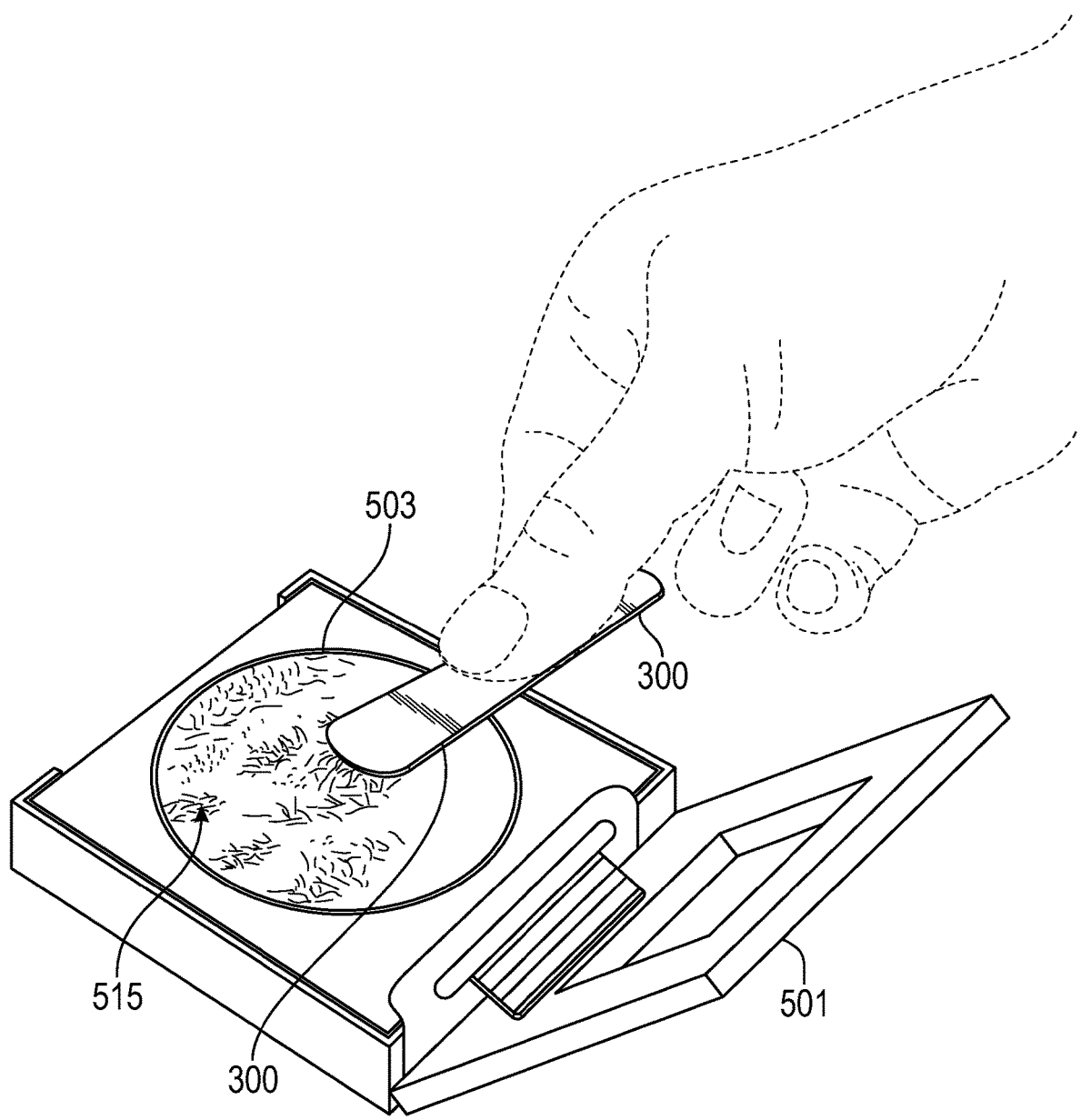
FIG. 5D may depict a spatula in use smoothing the broken makeup.

FIG. 5D may depict spatula 300 in use smoothing the broken-makeup 507, which may be damp-makeup 515. FIG. 5D may depict an implementation of step 425.

Figure 5E:
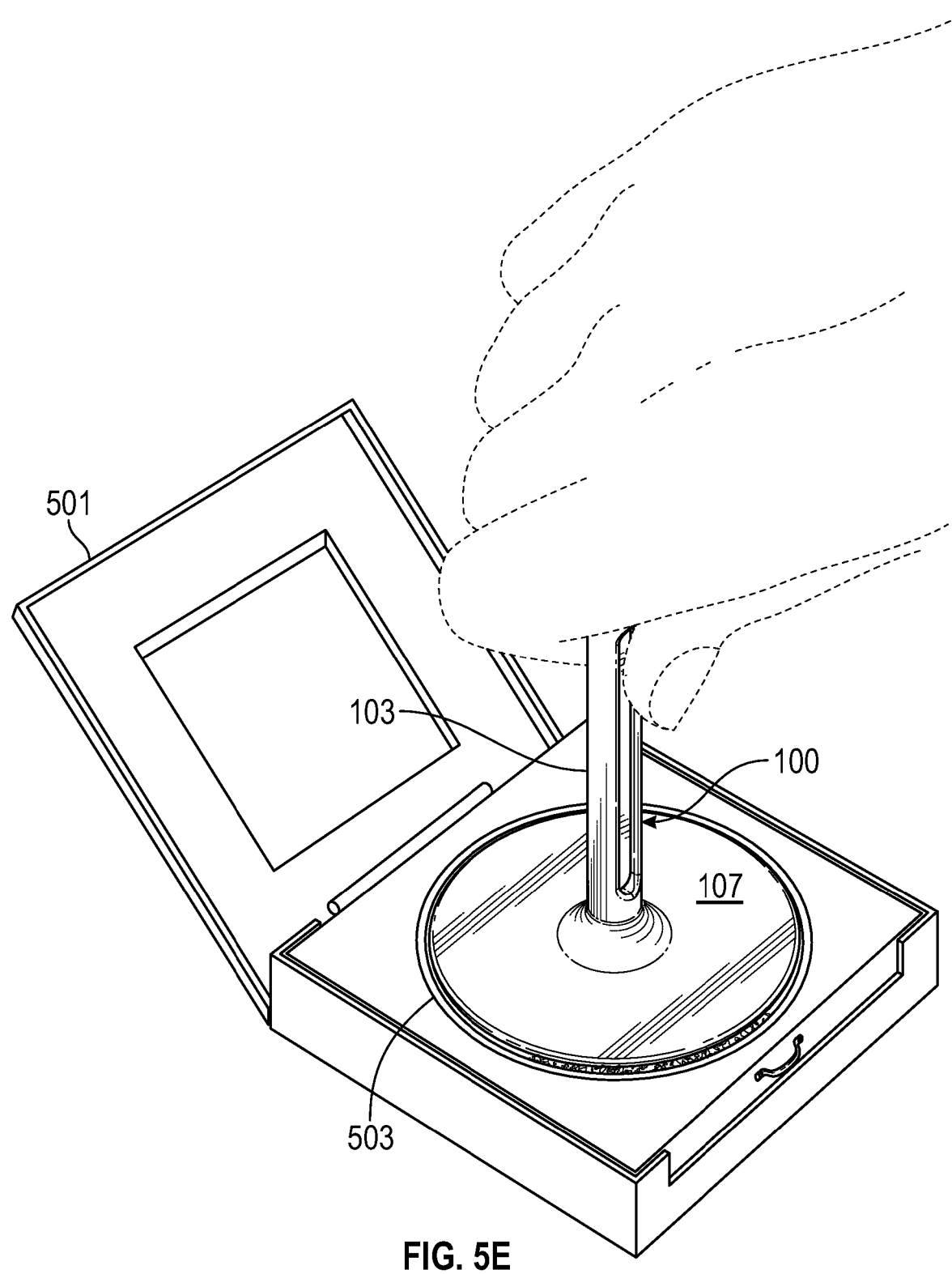
FIG. 5E may depict a makeup-repair-tool in use, pressing and compacting against makeup (including the broken makeup).

FIG. 5E may depict makeup-repair-tool 100 in use, pressing and compacting against makeup (including the broken makeup 507 or against the damp-makeup 515). FIG. 5E may depict an implementation of step 435. Note, had makeup pan 503 been square or rectangular shaped as opposed to the circular shape shown in FIG. 5E, then makeup-repair-tool 200 may have been used in the pressing and compacting shown in FIG. 5E.

Some embodiments of the invention may be characterized as a system for repairing makeup (or a system for refreshing makeup). In some embodiments, such a system may comprise a spatula 300; a container 511 with repair-mousse 513; and at least one makeup-repair-tool (e.g., 100 and/or 200). In some embodiments, the system may further comprise at least one makeup container 501 with makeup.

In some embodiments, the system may comprise a spatula 300; a container 511 with repair-mousse 513; makeup-repair-tool 100; and makeup-repair-tool 200. In some embodiments, the system may further comprise at least one makeup container 501 with makeup.

Some embodiments of the invention may be characterized as a kit for repairing makeup (or a kit for refreshing makeup). In some embodiments, such a kit may comprise a spatula 300; a container 511 with repair-mousse 513; and at least one makeup-repair-tool (e.g., 100 and/or 200). In some embodiments, the kit may further comprise at least one makeup container 501 with makeup.

In some embodiments, the kit may comprise a spatula 300; a container 511 with repair-mousse 513; makeup-repair-tool 100; and makeup-repair-tool 200. In some embodiments, the kit may further comprise at least one makeup container 501 with makeup.

Note with respect to the materials of construction, it is not desired nor intended to thereby unnecessarily limit the present invention by reason of such disclosure.

Makeup-repair-tools, systems for repairing makeup, kits for repairing makeup, and methods of repairing makeup; as well as for refreshing makeup, have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A makeup-repair-tool configured for repairing powder or mineral based makeup, wherein the makeup-repair-too 1 comprises:
    a first-press with a first-press-surface that is substantially flat and planar and configured for pressing against makeup such that the makeup that is pressed by the first-press-surface is left flat, planar, and compressed, wherein the first-press-surface is free of holes;
    a second-press with a second-press-surface that is substantially flat and planar and configured for pressing against different makeup such that the different makeup that is pressed by the second-press-surface is left flat, planar, and compressed, wherein the second-press-surface is also free of holes;
    a handle that is an elongate member that is disposed between the first-press and the second-press; wherein the handle is attached to the first-press and attached to the second-press; wherein the handle comprises at least one elongate slot that is an indented groove into the handle; wherein the at least one elongate slot has a longitude that is substantially parallel with a longitude of the elongate member of the handle; wherein the longitude of the at least one elongate slot is perpendicular to both the first-press-surface and the second-press-surface;
    wherein the handle has a transverse dimension, a width or a diameter, that is orthogonal to the longitude of the elongate member, wherein that transverse dimension is shorter than either a length of the first-press-surface or a length of the second-press-surface;
    wherein the transverse dimension of the handle is uniform and fixed along a length of the handle except where the handle attaches to the first-press and to the second-press;
    wherein the handle is longer than the second-press-surface;
    wherein the first-press-surface and the second-press-surface are both substantially manufactured from an electrostatically neutral material;
    wherein the first-press, the second-press, and the handle are all a single integral article of manufacture;
    wherein when a force is removably exerted upon the handle in a direction that is parallel with the longitude of the elongate member, the first-press-surface presses against the makeup; wherein when a different force, that is in an opposite direction of the force, is removably exerted upon the handle the second-press-surface presses against the different makeup.

2. The makeup-repair-tool according to claim 1, wherein the first-press comprises a first-non-press-surface; wherein the first-press-surface is disposed opposite from the first-non-press-surface; wherein at least portions of the first-press-surface removably contacts the makeup; and wherein the handle attaches to the first-press at at least one location of the first-non-press-surface; wherein the first-press-surface is substantially parallel with the first-non-press-surface.

3. The makeup-repair-tool according to claim 1, wherein the first-press-surface is one or more of substantially: smooth, rigid, or semi-rigid.

4. The makeup-repair-tool according to claim 2, wherein the first-press is defined and bound by a closed-perimeter that separates the first-press-surface from the first-non-press-surface.

5. The makeup-repair-tool according to claim 4, wherein this closed-perimeter is substantially shaped as: a circle, a polygon, a parallelogram, a rectangle, or a square.

6. The makeup-repair-tool according to claim 4, wherein this closed-perimeter is substantially shaped and sized to fit within a pan that is holding the makeup.

7. The makeup-repair-tool according to claim 1, wherein the handle is one or more of substantially: a structural member, a rigid member, a semi-rigid member, or a straight member.

8. The makeup-repair-tool according to claim 1, wherein the elongate member of the handle extends substantially orthogonally from a major surface of the first-press to a major surface of the second-press.

9. The makeup-repair-tool according to claim 1, wherein the first-press is disposed opposite from the second-press.

10. The makeup-repair-tool according to claim 1, wherein the handle comprises a second elongate slot that is opposing the at least one elongate slot; wherein these two opposing elongate slots each has a longitude this is substantially parallel with the longitude of the elongate member of the handle; wherein the second elongate slot is a second indented groove into the handle.

11. The makeup-repair-tool according to claim 1, wherein the first-press is larger than the second-press.

12. The makeup-repair-tool according to claim 1, wherein the second-press comprises a second-non-press-surface; wherein the second-press-surface is disposed opposite from the second-non-press-surface; wherein at least portions of the second-press-surface removably contacts the different makeup; and wherein the handle attaches to the second-press at at least one location of the second-non-press-surface; wherein the second-press-surface is substantially parallel with the second-non-press-surface.

13. The makeup-repair-tool according to claim 1, wherein the second-press-surface is one or more of substantially: smooth, rigid, or semi-rigid.

14. The makeup-repair-tool according to claim 12, wherein the second-press is defined and bound by a second-closed-perimeter that separates the second-press-surface from the second-non-press-surface.

15. The makeup-repair-tool according to claim 14, wherein this second-closed-perimeter is substantially shaped as: a circle, a polygon, a parallelogram, a rectangle, or a square.

16. The makeup-repair-tool according to claim 14, wherein this second-closed-perimeter is substantially shaped and sized to fit within a pan that is holding the different makeup.

17. A kit for repairing broken powder or mineral based makeup, comprising:
- a spatula for scraping and returning broken makeup back into a pan configured for holding the broken makeup;
- a container comprising repair-mousse configured for putting at least some of the repair-mousse onto the broken makeup;
- at least one makeup-repair-tool for pressing and compacting the broken makeup; wherein the at least one makeup-repair-tool comprises:
  - a first-press with a first-press-surface that is substantially flat and planar and configured for pressing against the broken makeup such that the broken makeup that is pressed by the first-press-surface is left flat, planar, and compressed, wherein the first-press-surface is free of holes;
  - a second-press with a second-press-surface that is substantially flat and planar and configured for pressing against different makeup such that the different makeup that is pressed by the second-press-surface is left flat, planar, and compressed, wherein the second-press-surface is also free of holes;
  - a handle that is an elongate member that is disposed between the first-press and the second-press; wherein the handle is attached to the first-press and attached to the second-press; wherein the handle comprises at least one elongate slot that is an indented groove into the handle; wherein the at least one elongate slot has a longitude that is substantially parallel with a longitude of the elongate member of the handle; wherein the longitude of the at least one elongate slot is perpendicular to both the first-press-surface and the second-press-surface;
- wherein the handle has a transverse dimension, a width or a diameter, that is orthogonal to the longitude of the elongate member, wherein that transverse dimension is shorter than either a length of the first-press-surface or a length of the second-press-surface; wherein the transverse dimension of the handle is uniform and fixed along a length of the handle except where the handle attaches to the first-press and to the second-press;
- wherein the handle is longer than the second-press-surface;
- wherein the first press-surface and the second-press-surface are both substantially manufactured from an electrostatically neutral material;
- wherein the first-press, the second-press, and the handle are all a single integral article of manufacture;
- wherein when a force is removably exerted upon the handle in a direction that is parallel with the longitude of the elongate member, the first-press-surface presses against the broken makeup; wherein when a different force, that is in an opposite direction of the force, is removably exerted upon the handle the second-press-surface presses against the different makeup.

18. The makeup-repair-tool according to claim 1, wherein the at least one elongate slot does not pass entirely through the handle such that the at least one elongate slot is not a hole through the handle.

* * * * *